United States Patent
Frias Goyenechea et al.

(10) Patent No.: US 11,116,907 B2
(45) Date of Patent: Sep. 14, 2021

(54) ACTUATION MECHANISMS FOR AUTOMATIC RECONSTITUTION AND PLUNGER EXPANSION IN DUAL CHAMBER SYRINGES

(71) Applicant: UNL Holdings LLC, New York, NY (US)

(72) Inventors: Oscar Frias Goyenechea, Philadelphia, PA (US); Richard A. Cronenberg, Mahwah, NJ (US)

( * ) Notice: Subject to any disclaimer, the term of this patent is extended or adjusted under 35 U.S.C. 154(b) by 840 days.

(21) Appl. No.: 15/789,644

(22) Filed: Oct. 20, 2017

(65) Prior Publication Data
US 2018/0110927 A1    Apr. 26, 2018

Related U.S. Application Data

(60) Provisional application No. 62/411,080, filed on Oct. 21, 2016.

(51) Int. Cl.
*A61M 5/20*    (2006.01)
*A61M 5/32*    (2006.01)
(Continued)

(52) U.S. Cl.
CPC ........ *A61M 5/2066* (2013.01); *A61M 5/2033* (2013.01); *A61M 5/284* (2013.01);
(Continued)

(58) Field of Classification Search
CPC .. A61M 5/2066; A61M 5/2033; A61M 5/284; A61M 5/31596; A61M 5/3234;
(Continued)

(56) References Cited

U.S. PATENT DOCUMENTS 9,327,083 B2    5/2016    Giambattista et al.
9,539,393 B2    1/2017    Johannesson et al.
(Continued)

OTHER PUBLICATIONS

International Search Report and Written Opinion for International Application No. PCT/IB2017/001274, entitled: "Actuation Mechanisms for Automatic Reconstitution and Plunger Expansion in Dual Chamber Syringes," dated Feb. 1, 2018 (12 pages).
(Continued)

*Primary Examiner* — Nathan R Price
*Assistant Examiner* — John A Doubrava
(74) *Attorney, Agent, or Firm* — Hamilton, Brook, Smith & Reynolds, P.C.

(57) ABSTRACT

An actuating device having integrated plunger is configured to be removably mounted to an automatic mixing device for a syringe. The actuating device includes lower and upper housings, a trigger member, a lockout ring, a mixing biasing member, a delivery plunger, a plunger biasing member, and a mixing plunger. The mixing plunger is releasably engaged with the trigger member in an initially locked state and engageable with at least one seal of the mixing device. The trigger member is operable to initiate decompression of the mixing biasing member and engagement of the mixing plunger with the at least one seal of the mixing device. The delivery plunger may also be activated to expand from a first, collapsed configuration to a second, expanded configuration by actuation of the trigger member.

17 Claims, 23 Drawing Sheets

(51) Int. Cl.
*A61M 5/315* (2006.01)
*A61M 5/28* (2006.01)

(52) U.S. Cl.
CPC ...... *A61M 5/31596* (2013.01); *A61M 5/3234* (2013.01); *A61M 2005/2006* (2013.01); *A61M 2005/31598* (2013.01)

(58) Field of Classification Search
CPC .............. A61M 5/1782; A61M 5/2448; A61M 5/3298; A61M 2005/2006; A61M 2005/31598; A61M 2005/2073; A61M 2005/2451; A61J 1/20; A61J 1/2003; A61J 1/2096
See application file for complete search history.

(56) References Cited

U.S. PATENT DOCUMENTS

| | | |
|---|---|---|
| 9,649,442 B2 | 5/2017 | Bendek et al. |
| 2013/0060232 A1* | 3/2013 | Adlon ................ A61M 5/2066 604/506 |
| 2014/0358091 A1* | 12/2014 | Johannesson ....... A61M 5/2066 604/187 |
| 2016/0250418 A1 | 9/2016 | Olson |

OTHER PUBLICATIONS

International Preliminary Report on Patentability for International Application No. PCT/IB2017/001274, entitled: "Actuation Mechanisms for Automatic Reconstitution and Plunger Expansion in Dual Chamber Syringes," dated Apr. 21, 2020 (6 pages).

* cited by examiner

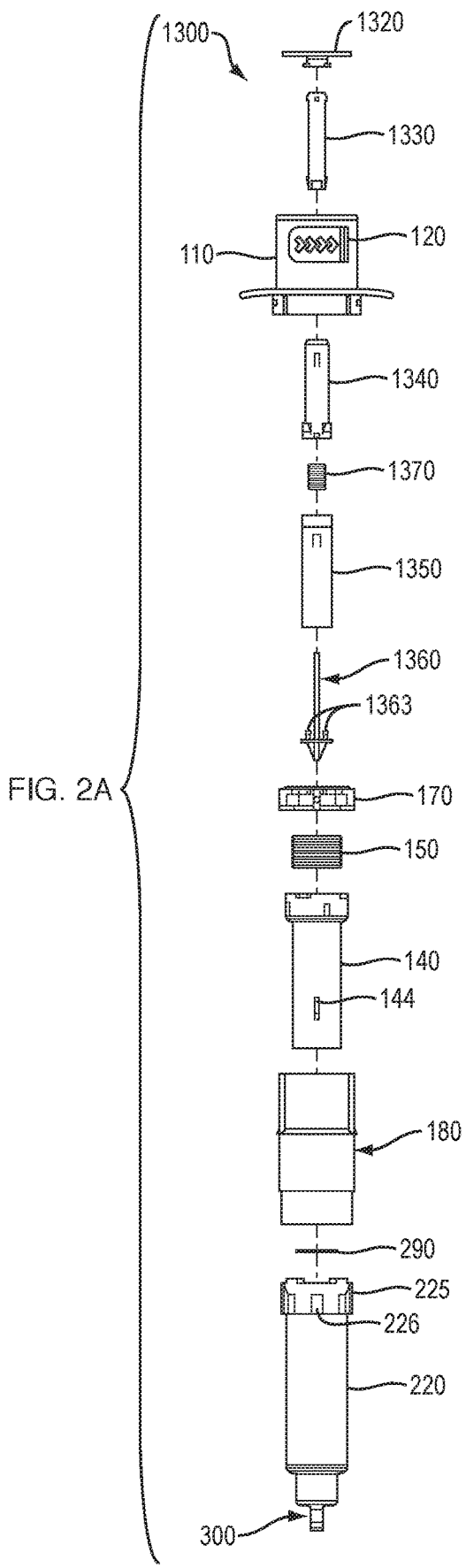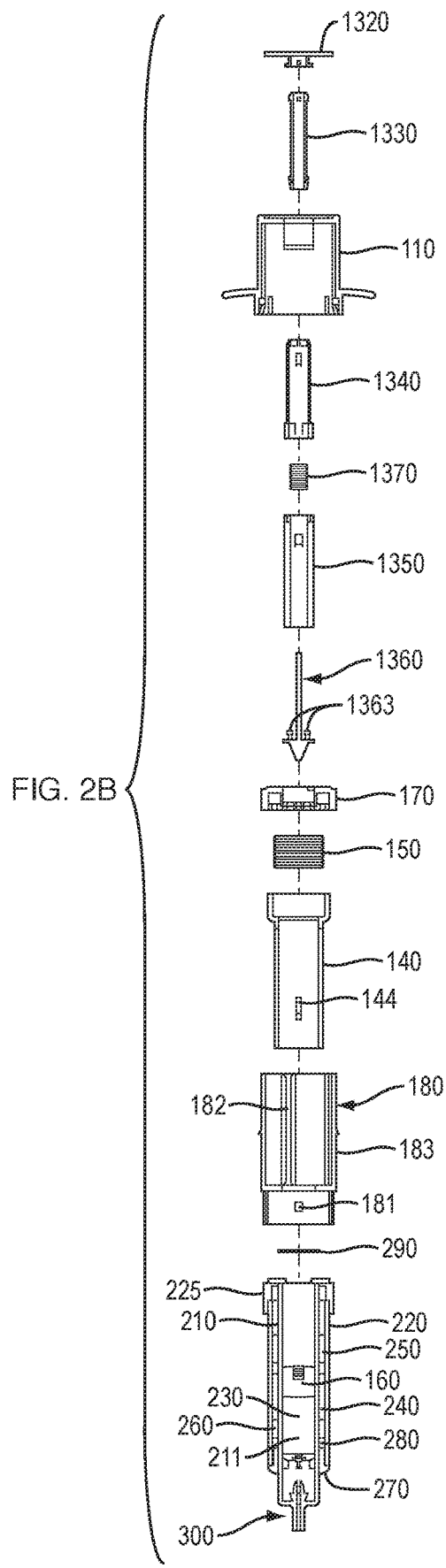

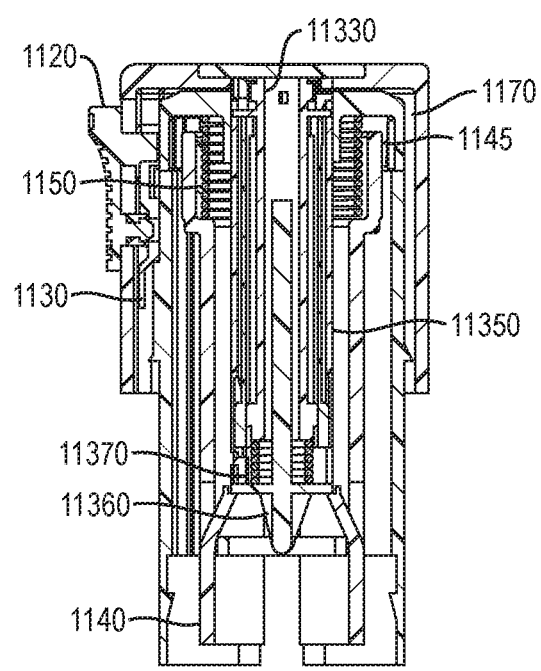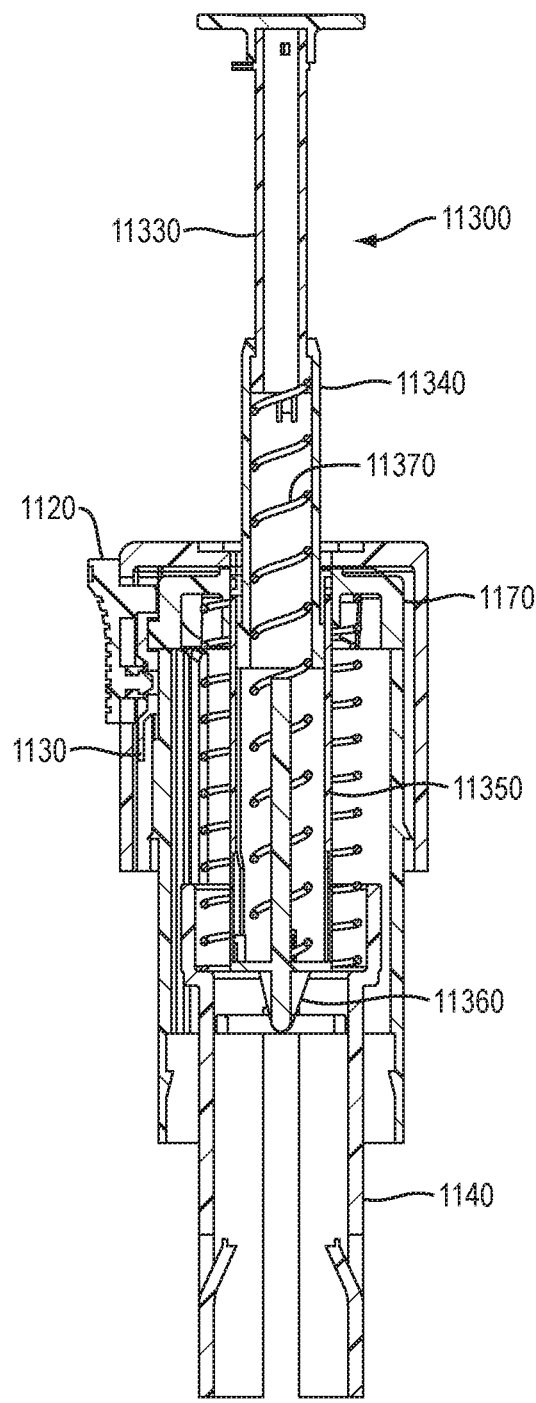
FIG. 19A
FIG. 19B

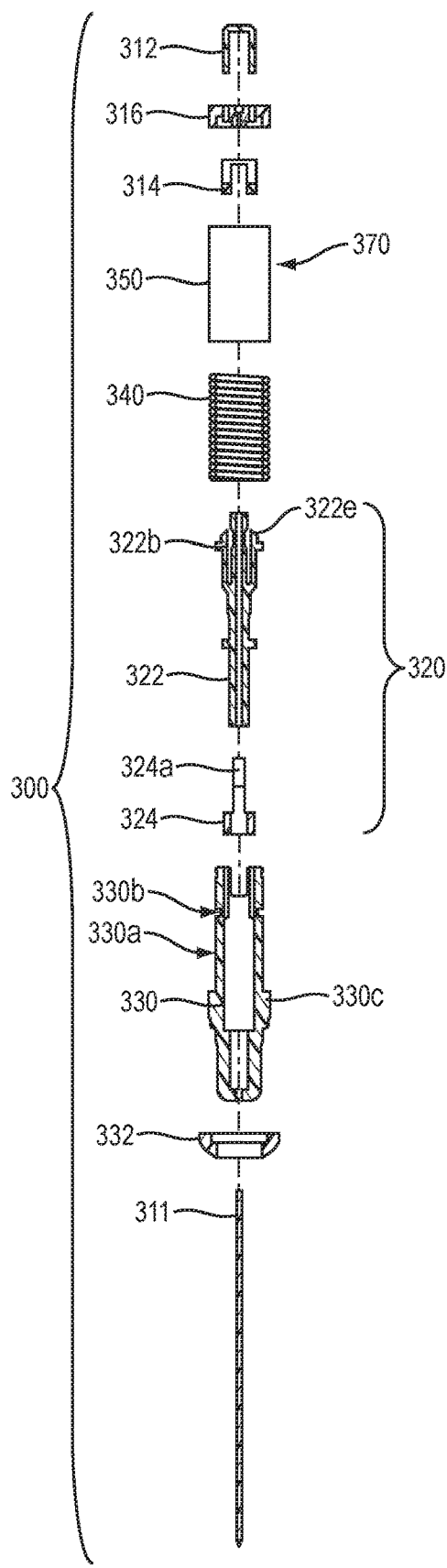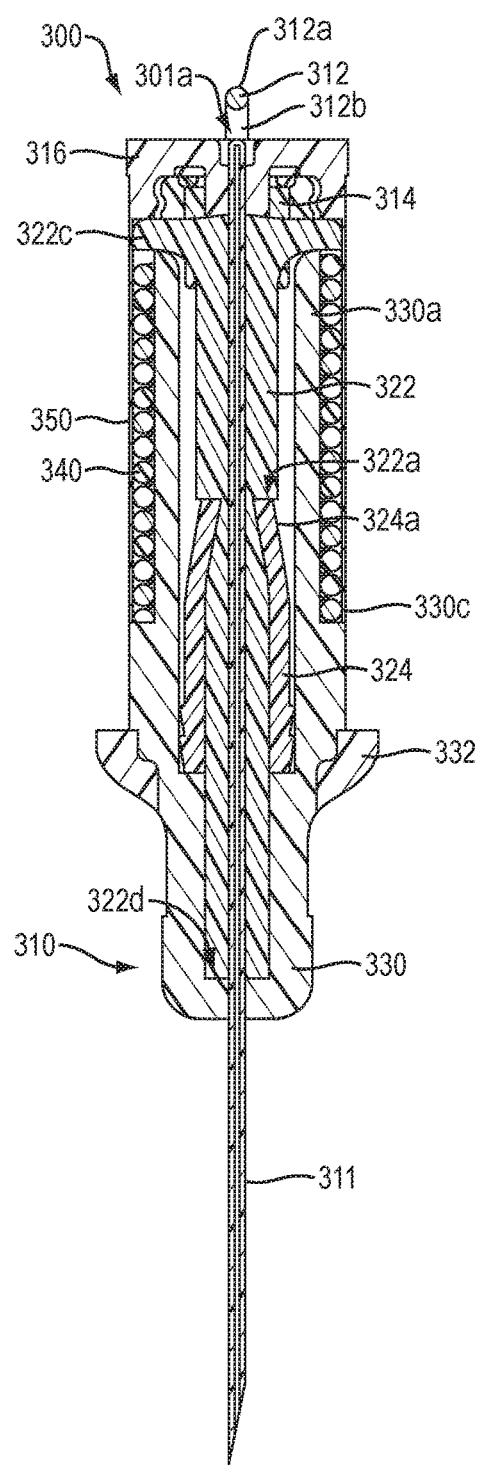
FIG. 22A
FIG. 22B

ACTUATION MECHANISMS FOR AUTOMATIC RECONSTITUTION AND PLUNGER EXPANSION IN DUAL CHAMBER SYRINGES

RELATED APPLICATION

This application claims the benefit of U.S. Provisional Application No. 62/411,080 filed on Oct. 21, 2016. The entire teachings of the above application are incorporated herein by reference

BACKGROUND

It is known to provide syringes that comprise a mixing device for mixing deliverable substances prior to injection. This allows, for example, a diluent to be added to a dehydrated, lyophilized, desiccated or powdered active substance immediately prior to injection, which is particularly useful for substances that are subject to degradation or loss of activity when stored in a hydrated form.

The majority of mixing devices for syringes utilize sequential chambers, wherein the syringe has one barrel having a first proximal chamber and a second distal chamber separated by, for example, a membrane or elastomeric seal. A number of such sequential-chamber mixing syringes utilize a bypass protrusion at a section of the barrel to enable fluid in the proximal chamber to bypass the dividing membrane and mix with the fluid or powder in the distal chamber.

However, some mixing syringes utilize concentric barrel configurations. The concentric barrel mixing syringes to date, however, require complex assemblies, multiple operation steps by the user, or other particular nuances that make them difficult to manufacture, assemble, or operate. For example, some existing concentric barrel mixing syringes require concentric inner and outer barrels that are selectively rotatable with respect to each other, and require one or more sealing rings which contain a passage means therein. The barrels must be rotated to align a hole in the inner barrel with the passage means in a sealing ring. The passage means in the sealing ring includes a radially extending opening through the sealing ring and a groove extending longitudinally of the sealing ring from the radially extending opening. This arrangement being such that the groove connects the outer barrel with the radially extending opening and the radially extending opening selectively connects the groove with the hole in the inner barrel. This enables flow of fluid from the outer barrel into to the inner barrel to thereby mix the fluid with a substance in the inner barrel. Such configurations require complex components and cumbersome requirements for the user to operate the device.

Other concentric barrel designs utilize outer and inner telescopic tubular elements seated inside a barrel and coaxial with the longitudinal axis. The outer tubular element and barrel form a chamber which holds a reservoir of liquid. The outer tubular element has a fluid passageway therein that allows the liquid to flow from the chamber into the inner tubular element. The inner tubular element has an end nearby the injection port with a seal thereon that has an orifice therein. This inner tubular element receives the end of the plunger with the resilient seal thereon. Accordingly, such mixing syringe configurations require three tubular elements, with the outer and inner concentric chambers residing inside a third barrel.

There are numerous complexities associated with the use of concentric barrels for mixing syringe configurations. In addition to those described above, mixing syringes utilizing concentric barrels must also address factors such as maintenance of container sterility, interaction of components for sealing, venting requirements, and distribution of internal forces, among others. Some dual chambered syringes have concentric inner and outer barrels that form an annular space to hold a fluid and utilize one or more apertures between the inner and outer barrels to enable flow of a liquid from the annular space into the inner barrel and thereby mix the liquid with a substance in the inner barrel. The liquid is forced from the annular into the inner barrel by depression of a plunger slidably movable in the annular space. First and second sealing bands are slidably received about the inner barrel in the annular space and are mutually spaced therealong. The position of the sealing bands can dictate how sterility of the fluid path is maintained, how internal forces are distributed, and how venting occurs. For example, both of the sealing bands may be initially positioned above the aperture to form a sealed annular volume for the first liquid component. Because of this arrangement, the aperture also must act as a vent to enable any air in the annular space distal to the second sealing band, which space must be sterilized, to be expelled via the aperture upon depression of the plunger. This venting requirement may cause difficulties and require additional equipment and processing steps, such as requiring filling the inner chamber under vacuum to remove all air from the inner chamber and the distal portion of the outer barrel below the second reconstitution seal.

Generally, prior art mixing devices comprising concentric barrels are complicated in structure and often require rotation of the barrels to align one or more apertures that enable a flow of a liquid substance from one chamber into another. Further to this, various sterility, sealing and venting arrangements have been used which have serious limitations in terms of ease of manufacture and operation of the mixing device.

SUMMARY

It is therefore an object of the invention to provide an automatic mixing device and/or a syringe comprising the automatic mixing device that alleviates one or more of the problems associated with prior art mixing devices and/or syringes, such as those referred to above.

An aspect of the invention provides an actuating device removably mountable to a mixing device for a syringe, said mixing device comprising one or more seals, the actuating device comprising a lower housing releasably connectable to the mixing device, an upper housing engaged with the lower housing, a trigger member, a lockout ring, a mixing biasing member, a delivery plunger, an expansion biasing member, and a mixing plunger releasably engaged with the trigger member in an initially locked state and engageable with at least one of the one or a plurality of seals of the mixing device, wherein said trigger member is operable to initiate said biasing member to facilitate depression of said mixing plunger when engaged with said at least one of the one or more seals. The trigger member may also be operable to initiate expansion of the delivery plunger from an initial, collapsed configuration to an expanded configuration.

Another aspect of the invention provides an automatic mixing device comprising an actuating device removably mountable to the mixing device for a syringe, said mixing device comprising one or more seals, the actuating device comprising a lower housing releasably connectable to the mixing device, an upper housing engaged with the lower housing, a trigger member, a lockout ring, a mixing biasing member, a delivery plunger, an expansion biasing member, and a mixing plunger releasably engaged with the trigger member in an initially locked state and engageable with at least one of the one or a plurality of seals of the mixing device, wherein said trigger member is operable to initiate said biasing member to facilitate depression of said mixing plunger when engaged with said at least one of the one or more seals. The trigger member may also be operable to initiate expansion of the delivery plunger from an initial, collapsed configuration to an expanded configuration.

Yet another aspect of the invention provides an automatic mixing syringe comprising a mixing device and an actuating device removably mounted thereto and a needle assembly, said mixing device comprising one or more seals, the actuating device comprising a lower housing releasably connectable to the mixing device, an upper housing engaged with the lower housing, a trigger member, a lockout ring, a mixing biasing member, a delivery plunger, an expansion biasing member, and a mixing plunger releasably engaged with the trigger member in an initially locked state and engageable with at least one of the one or a plurality of seals of the mixing device, wherein said trigger member is operable to initiate said biasing member to facilitate depression of said mixing plunger when engaged with said at least one of the one or more seals. The trigger member may also be operable to initiate expansion of the delivery plunger from an initial, collapsed configuration to an expanded configuration.

Suitably, the actuating device is mountable or mounted to the mixing device in an initially locked state. Suitably, the lockout ring is rotatable clockwise and/or anticlockwise to initiate said biasing member to facilitate depression of said mixing plunger when engaged with said at least one seal. The lockout ring may be rotatably engaged with the trigger member such that the user may rotate the trigger member and thereby initiate mixing. Alternatively, the lockout ring may have a rotational bias such that, in an initial configuration, the lockout ring is prevented from rotating. The user may allow the lockout ring to rotate by displacing a trigger member.

In at least one embodiment, the delivery plunger may comprise one or more telescoping aspects such the delivery plunger may be transformed from an initial, collapsed configuration to an expanded configuration by translation of the trigger member. Expansion of the delivery plunger may be caused by an expansion biasing member which in the initial, collapsed configuration is in a compressed or energized state. The expansion biasing member may be restricted from decompressing or de-energizing by engagement of a portion of the delivery plunger with the lockout ring. In at least one embodiment a flange of the delivery plunger cap interacts with a protrusion on the lockout ring to prevent expansion of the biasing member. Alternatively, the delivery plunger may be prevented from expanding by an interaction between the inner telescoping sleeve and the outer telescoping sleeve. For example, an extension of the inner telescoping sleeve may initially be disposed in a recess of the outer sleeve. Rotation of the lockout ring may be transferred to the outer sleeve, thereby releasing the recess from engagement with the extension of the inner sleeve and allowing expansion of the delivery plunger.

In an embodiment, the mixing plunger comprises one or more protrusions initially engaged with the lockout ring in the initial locked state. Preferably, this engagement is through engageable interaction between the protrusions or portions thereof and a surface of the lockout ring. Suitably, the mixing biasing member is initially retained in an energized state between the lockout ring and the mixing plunger.

In at least one embodiment, the mixing biasing member is initially bearing upon a plateau of the mixing plunger. Upon rotation of the lockout ring, the mixing plunger is disengaged from the lockout ring and caused to translate axially by expansion of the mixing biasing member from its energized state. Axial translation of the mixing plunger in the distal direction causes the axial translation of said at least one seal of the mixing device. Preferably said at least one seal is a proximal seal. Preferably, the mixing plunger comprises one or more sleeve members. Axial translation of the mixing plunger in the distal direction causes the sleeve members to bear upon and axially translate said at least one seal of the mixing device, as described above In at least one embodiment, the mixing device and/or the automatic mixing syringe comprises a sealing membrane that maintains the sterility of the mixing device prior to operation, wherein said membrane is removable by or during the operation of the actuating device, mixing device and/or the automatic mixing syringe. Preferably, the sealing membrane is removable. The sealing membrane may be manually removed such as through a pull-tab motion by the user. In another embodiment, the sealing membrane may be removed by indirect action by the user, such as by user activation of the actuating device. In one such embodiment, user activation of the actuating device causes a component of the actuating device, such as the sleeve members of the mixing plunger, to axially translate and at least partially remove or puncture the membrane from the mixing device. Additionally or alternatively, a component of the actuating device, such as a distal tip of the delivery plunger, may be used to pierce the membrane. Such a configuration permits the sterility of the mixing device to be maintained prior to operation of the actuating device or use of the automatic mixing syringe. In a preferred form, the sealing membrane is discoidal and puncturable by the delivery plunger. Notably, the delivery plunger is a component of the actuating device. Such a configuration permits the sterility of the mixing device to be maintained prior to operation of the actuating device, mixing device or use of the automatic mixing syringe.

In a particular embodiment, the mixing device further comprises an outer barrel and an inner barrel in a substantially coaxial relationship. Preferably, the outer barrel and the inner barrel are concentric. Suitably, the inner barrel and the outer barrel are non-rotatable with respect to each other. Suitably, the actuating device is removably mountable or mounted to the outer barrel. In one particular embodiment, the outer barrel comprises a barrel extension to which the actuating device is removably mountable or mounted. Removable mounting may be by way of a snap fit or interference fit, a screw thread or a bayonet coupling, although without limitation thereto. The barrel extension may be mounted to the outer barrel, or integrally formed with the outer barrel. The barrel extension may, optionally, include finger flanges or grips, or may alternatively have optional finger flanges or grips connected thereto.

In an embodiment, the inner barrel comprises an inner chamber. In an embodiment, an outer chamber is located in an annular space between the inner barrel and the outer barrel. According to this embodiment, the one or more seals of the mixing device are axially moveable within the outer chamber. Suitably, said mixing device is capable of comprising a plurality of mixing substances. Suitably, at least a first mixing substance is locatable in the outer chamber and at least a second mixing substance is locatable in an inner chamber in said inner barrel. In an embodiment, the inner barrel comprises one or more fluid paths through which the first mixing substance can enter the inner chamber in the inner barrel to thereby form a mixture with the second mixing substance.

The one or more fluid paths may comprise one or more apertures, holes, bores, ports, pass-throughs or conduits. These may be of any suitable shape, configuration, arrangement and/or number. Preferably, the fluid path comprises a plurality of apertures. The apertures may be radial bores (i.e., normal to the axis of the barrel), angular bores (i.e., at an angle to axis of the barrel), helical (e.g., an angular and radial path as it traverses the thickness of the barrel wall), or any number of other configurations. The number and placement of the apertures, in locational spacing and arrangement, may also be adjusted for the desired mixing characteristics. As such, these parameters of the apertures may be configured to promote the desired mixing, dilution, and other fluid flow characteristics of the mixing syringe. Suitably, the mixing device may comprise one or more components described in International Publication WO2013/020170, which is incorporated by reference in its entirety for all purposes.

The first and second mixing substances may comprise one or more fluids or one or more solids. The first mixing substance locatable in the outer chamber may be a fluid. The fluid may be a pharmaceutically active fluid or a pharmaceutically inactive fluid, such as a diluent. The second mixing substance locatable in the inner chamber may be a pharmaceutically active solid or a pharmaceutically active or inactive fluid. In one embodiment, the inner chamber contains a pharmaceutically active solid and the outer chamber contains a pharmaceutically inactive diluent, such as water, whereby entry of the diluent through the one or more fluid paths from outer chamber into the inner chamber facilitates mixing with the pharmaceutically active solid. The interaction between the diluent and the pharmaceutically active solid enables reconstitution of the pharmaceutically active solid for subsequent delivery to a patient. In another embodiment, the inner chamber contains a pharmaceutically active solid and the outer chamber contains a pharmaceutically active fluid, whereby entry of the fluid through the one or more fluid paths from the outer chamber into the inner chamber facilitates mixing with the pharmaceutically active solid in the inner chamber. The interaction between the pharmaceutically active fluid and the pharmaceutically active solid enables reconstitution of the pharmaceutically active solid for subsequent delivery to a patient. In yet another embodiment, the inner chamber contains a first pharmaceutically active fluid and the outer chamber contains a second pharmaceutically active fluid, whereby entry of the first pharmaceutically active fluid through the one or more fluid paths from the outer chamber into the inner chamber facilitates mixing with the second pharmaceutically active fluid in the inner chamber. While the operation of the actuating device, mixing device, and the automatic mixing syringe are described with reference to a fluid moving from an outer chamber to an inner chamber, such description is meant only as an exemplary fluid transfer between the outer and inner chambers and the opposite is also possible. Accordingly, the present invention also provides for devices and syringes which facilitate the transfer of fluids from the inner chamber to the outer chamber. Additionally, the fluid transfer between inner and outer chambers can be configured to occur once or repeatedly, due to the "closed system" configuration made possible by the embodiments of the present invention. In another of these configurations, the interaction between the first pharmaceutically active fluid and the second pharmaceutically active fluid enables mixing of the pharmaceutically active fluids for subsequent delivery to a patient. Similarly a liquid diluent and a liquid pharmaceutically active fluid may be stored and mixed to dilute the pharmaceutically active fluid for subsequent delivery to a patient. Accordingly, the mixing device may facilitate the storage of multiple component pharmaceutical substances in the outer and inner chambers, thereby maintaining the stability and efficacy of the pharmaceutical substances during transport and over prolonged periods of storage.

In a further embodiment, the mixing device comprises one or more vents in fluid communication with said outer chamber. Preferably, the one or more vents are operable to facilitate exit of air from the outer chamber to atmosphere when the mixing plunger and distal seal are slidably moved in the outer chamber. The one or more vents may be integrally formed in said outer barrel or may be a vent cap mounted or affixed to said inner and/or outer barrel. In either embodiment, conduits, holes, porous membranes, collapsible components and the like may be utilized. For example, in at least one embodiment the vent cap is a plastic vent cap comprising one or more vent conduits, which plastic vent cap closes the outer chamber at the distal end of the outer barrel while permitting air to pass through the one or more vent conduits to atmosphere upon depression of the mixing plunger.

Suitably, the mixing device comprises said at least one seal located in said outer chamber which is capable of axial movement from a first position in sealing engagement with said one or more fluid paths in the inner barrel to a second position at least partly between said one or more fluid paths and said one or more vents. In a preferred form, the mixing device comprises a plurality of seals. In one particular form, the plurality of seals comprises a proximal seal and a distal seal. Suitably, said at least one seal is the distal seal. In a preferred embodiment, the plurality of seals comprises: a proximal seal engageably or connectably coupled to, connectable or affixed to, or otherwise adjacent to the one or more sleeves of the mixing plunger and slidably moveable in the outer chamber; and said distal seal initially in a first position in sealing engagement with said one or more fluid paths in the inner barrel and slidably moveable in the outer chamber from sealing engagement with the one or more fluid paths to a second position intermediate or at least partly between said one or more fluid paths and said vent. The movement of the one or more sleeve members of the mixing plunger causes movement of the proximal seal to which the sleeve members are engaged or adjacent to. This movement is relayed to the first mixing substance in the outer chamber and, similarly, to the distal seal. In at least one embodiment, the movement of the one or more sleeve members, the proximal seal and, accordingly, the first mixing substance in the outer chamber is relayed to the distal seal by pneumatic pressure or force created in the first mixing substance by the motion of the mixing plunger seal. Accordingly, axial movement of the one or more sleeve members indirectly (i.e., without needing direct contact) facilitates axial movement of the distal seal to said second position.

One or more embodiments of the present invention include a vent cap which may optionally have internal vent cap features which facilitate the desired positioning of the distal seal during operation of the mixing device. The internal vent cap features may be, for example, posts, prongs, flex arms, or the like which are configured to correctly position the distal seal upon translation within the outer chamber, with reference to the one or more apertures, to enable substantially all of the first substance within the outer chamber to be passed-through to the inner chamber.

The fluid paths between the outer and inner chambers are desired to remain open to allow movement of the first substance until substantially all of the first substance is pushed out of the outer chamber by the mixing plunger seal. This may be achieved by the compressibility of the seals themselves. Additionally or alternatively, the dimensions and the flexing capabilities of the internal vent cap features may be configured to align the distal seal with the apertures to ensure that substantially all of the first substance within the outer chamber is passed-through to the inner chamber.

Suitably, the one or more sleeve members of the actuating device are axially moveable within the outer chamber between the outer barrel and the inner barrel. The one or more sleeve members of the mixing plunger may facilitate entry of the at least first mixing substance into the inner chamber in the inner barrel and to facilitate axial movement of the distal seal from a first position in sealing engagement with said one or more fluid paths in the inner barrel to said second position intermediate or at least partly between said one or more fluid paths and said vent, as described above.

The syringe may be utilized for storing, transporting, mixing, and injecting one or more mixing substances to treat a patient. As will be described further below, the syringe may further contain safety features which retract the needle after use, providing desirable needle-stick prevention, and prevent re-use of the syringe. Suitably, the plunger of the actuating device is slidably moveable within the inner barrel of the mixing device to thereby facilitate delivery of the mixed substances or mixture to a user, patient or other recipient.

In an embodiment, the automatic mixing syringe may comprise a retractable needle or needle assembly, referred to herein as a "retractable syringe". In a further embodiment, the delivery plunger may be utilized to activate a retraction mechanism of the automatic mixing syringe.

It will be appreciated that the retractable syringe may comprise any needle retraction mechanism that is operable with the invention disclosed herein. By way of example, the needle retraction mechanism may be as described in International Publication WO2006/119570, International Publication WO2006/108243, International Publication WO2009/003234 and International Publication WO2011/075760, and/or U.S. Pat. No. 8,702,653 and International Application PCT/US2014/024781, although without limitation thereto.

In one broad form, the automatic mixing syringe is a retractable syringe that comprises a needle assembly mounted thereto, such as at a distal end of an inner chamber of the mixing device or syringe, wherein the needle assembly comprises an energized biasing member (such as a compressed spring), release of said biasing member facilitates retraction of the retractable needle. In a particular embodiment, the retractable needle is a component of a needle retraction mechanism that includes a needle subassembly including a cannula and a needle-over-mold through which the cannula extends. The needle retraction mechanism may be at least partly housed within a barrel adapter mounted to a barrel tip. Suitably, the retractable needle is adapted to move from an injection position in which the needle extends from a distal end of the barrel or barrel tip to a retracted position in which the needle is disposed at least partly within the barrel or barrel tip. An actuator subassembly includes a needle seal, a push bar and at least one actuating surface, the push bar being disposed at least partially proximal to the needle seal. The actuator subassembly further comprises at least one biasing member (e.g., a compressed spring) and an actuable locking arrangement disposed to maintain the biasing member in an energized position when the locking arrangement is locked. Suitably, actuation of release of the locking arrangement releases the biasing member, the biasing member being disposed to move the needle from the injection position to the retracted position when the biasing member is released from the energized position. Suitably, the locking arrangement is actuable by depression of the plunger and contact of the plunger seal with the push bar. A non-limiting example of this embodiment is described in International Application PCT/US2014/024781.

In an alternative embodiment of this broad form, the needle assembly may be similar to that disclosed in U.S. Pat. No. 8,702,653 which does not require a needle body and which activates retraction of the cannula through contact between the delivery plunger seal and a needle seal.

Preferably, the needle assembly may further comprise a needle seal that retains the retractable needle, wherein the cannula of the retractable needle passes through the needle seal to permit delivery of the mixed substances or mixture to a user, patient, or other recipient. Suitably, the retractable syringe comprises one or more delivery plunger locking systems to prevent axial translation of the needle in the distal direction after retraction of the delivery plunger seal and the needle engaged therewith.

As described herein, the protrusions of the mixing plunger co-operate with the lockout ring to maintain the mixing biasing member in an initially energized state. Disengagement of the one or plurality of protrusions from the lockout ring facilitates release of stored energy from the mixing biasing member. In an embodiment, the mixing plunger further comprises bosses that engage guide tracks in an inner wall of the lower housing, such as during axial movement of the mixing plunger relative to the housing. In an embodiment, a body portion of the mixing plunger comprises one or more guides that slidably engage grooves in an inner wall of the housing, such as during axial movement of the mixing plunger relative to the housing. The projections or guides, and their slidable engagement with the inner wall of the housing, may be utilized to prevent axial rotation of the mixing plunger with reference to the housing.

In yet another aspect, the invention provides a method of assembling a syringe comprising an automatic mixing device including the step of removably mounting an actuating device to a mixing device of the syringe so that a trigger member of the actuating device is operable to actuate depression of a mixing plunger seal of the mixing device. In one embodiment, the method includes the step of releasably connecting or coupling a housing of the actuating device to an outer barrel of the mixing device. In one embodiment, the method further includes, prior to step (i), affixing a vent cap comprising the one or more vents to a portion of the inner barrel that is located distally of the one or more apertures. Preferably, the distal end of the outer barrel is connected to the vent cap. In a further embodiment, the method further includes the step of attaching a removable or pierceable membrane to the proximal end of the inner barrel of the mixing device prior to attachment of the actuating device to the mixing device. In a preferred embodiment, the removable or pierceable membrane is attached in a manner such that it is removed automatically by operation of the sleeve of the actuating device, i.e., axial translation of the sleeve in the distal direction. Preferably, the method further includes the step of inserting a needle assembly into the inner chamber located distally of the one or more fluid paths.

In a further aspect, the invention provides a method of manufacturing a syringe including the step of removably mounting an actuating device to a mixing device mounted to a syringe.

In a still further aspect, the invention provides a method of operating a syringe comprising an automatic mixing device, said method including the steps of:
(i) operating an actuating device of the automatic mixing device to facilitate mixing a plurality of substances;
(ii) connecting a plunger of the actuating device to a delivery plunger seal of the mixing device;
(iii) operating the plunger to deliver the substances mixed at step (i) to a recipient.

Preferably, operation of the actuating device removes or pierces a membrane from attachment to the mixing device. In one embodiment, the method includes the step of unlocking the plunger prior to step (iii). Unlocking the plunger may occur between steps (i) and (ii) in at least one embodiment or between steps (ii) and (iii) in other embodiments of the invention.

In another embodiment, the method of operating a syringe comprising an automatic mixing device further includes: (iv) activating a needle retraction mechanism to retract the needle into the syringe. Preferably, the activation of the needle retraction mechanism occurs after substantially all of the substances are delivered to the recipient.

In a further embodiment, an actuating device includes a lower housing configured to be releasably connectable to a mixing device for a syringe and an upper housing engaged with the lower housing. The device further includes a trigger member, a lockout ring, a mixing biasing member, a delivery plunger, and a mixing plunger. The mixing plunger is releasably engaged with the trigger member in an initially locked state and engageable with at least one seal of the mixing device. The trigger member is operable to initiate decompression of the mixing biasing member and engagement of the mixing plunger with the at least one seal of the mixing device.

The lockout ring can be rotatably engaged with the trigger member and configured to permit decompression of the mixing biasing member upon rotation. For example, the mixing plunger can include one or more protrusions initially engaged with a surface of the lockout ring in the initially engaged state. The protrusions can be configured to disengage from the surface upon rotation of the lockout ring, thereby permitting the mixing biasing member to decompress from an energized to de-energized state. The mixing plunger can further include one or more sleeve members that are configured to bear upon and axially translate at least one seal of the mixing device.

The actuating device can further include a plunger biasing member. The trigger member can be further operable to initiate decompression of the plunger biasing member and expansion of the delivery plunger from an initial, collapsed configuration to an expanded configuration. For example, the delivery plunger can include one or more telescoping aspects configured to expand upon expansion of the plunger biasing member. The delivery plunger can include a plunger cap that includes a flange initially engaged with a protrusion of the lockout ring, the flange configured to disengage from the protrusion upon rotation of the lockout ring.

The actuating device can be mountable or mounted to the mixing device in an initially locked state, providing for ease of manufacturing.

An automatic mixing device includes an actuating device and a mixing device that includes an outer barrel and an inner barrel in a substantially coaxial relationship. At least one seal is located in an annular space between the inner barrel and the outer barrel and that is axially moveable within the annular space.

A sealing membrane can be included in the mixing device to maintain sterility of the mixing device. The sealing membrane can be removable by or during operation of the actuating device. For example, sleeve members of the mixing plunger can be configured to at least partially remove or puncture the sealing membrane upon axial translation. In addition, or alternatively, a distal tip of the delivery plunger can be configured to pierce the sealing membrane upon axial translation.

The outer barrel of the mixing device can include a barrel extension to which the actuating device may be removably mountable or mounted. The inner barrel can include one or more fluid paths that are configured to provide fluid communication between an inner chamber of the inner barrel and an outer chamber located in the annular space between the inner barrel and the outer barrel. Mixing substances can be included in each of the outer chamber and inner chamber, as provided by, respectively the inner barrel and an annular space between the inner and outer barrels. The fluid path can be configured to permit a first mixing substance, located in an outer chamber, to enter the inner chamber containing a second mixing substance upon displacement of the at least one seal. At least one of the first mixing substance and the second mixing substance can be a fluid and at least one of the first mixing substance and the second mixing substance can be an active pharmaceutical. The automatic mixing device enables reconstitution or mixing of the active pharmaceutical(s).

The automatic mixing device can further include at least one vent in fluid communication with the annular space. The vent can be operable to facilitate exit of air from the annular space to the atmosphere when the mixing plunger and the at least one seal are axially translated within the annular space.

An automatic mixing syringe includes a mixing device and an actuating device, as well as an end fitment. The end fitment can include or be adapted to receive, for example, a retractable needle assembly, to provide for delivery of the mixed substances.

BRIEF DESCRIPTION OF THE DRAWINGS

Non-limiting embodiments of the invention are described herein with reference to the following drawings wherein:

FIG. 2A shows an exploded view of the actuating device shown in FIG. 1;

FIG. 2B shows a cross-sectional exploded view of the actuating device shown in FIG. 1;

FIG. 19A shows a cross-sectional view of an actuating device according to at least one embodiment of the present invention in an initial configuration;

FIG. 19B shows a cross-sectional view of an actuating device according to at least one embodiment of the present invention in an activated configuration;

FIG. 22A shows an exploded sectional view of an embodiment of a needle retraction mechanism comprising a needle assembly having biasing member comprising a single spring;

FIG. 22B shows a sectional view embodiment of a needle retraction mechanism comprising a needle assembly having a biasing member comprising a single spring;

DETAILED DESCRIPTION

Figure 1:
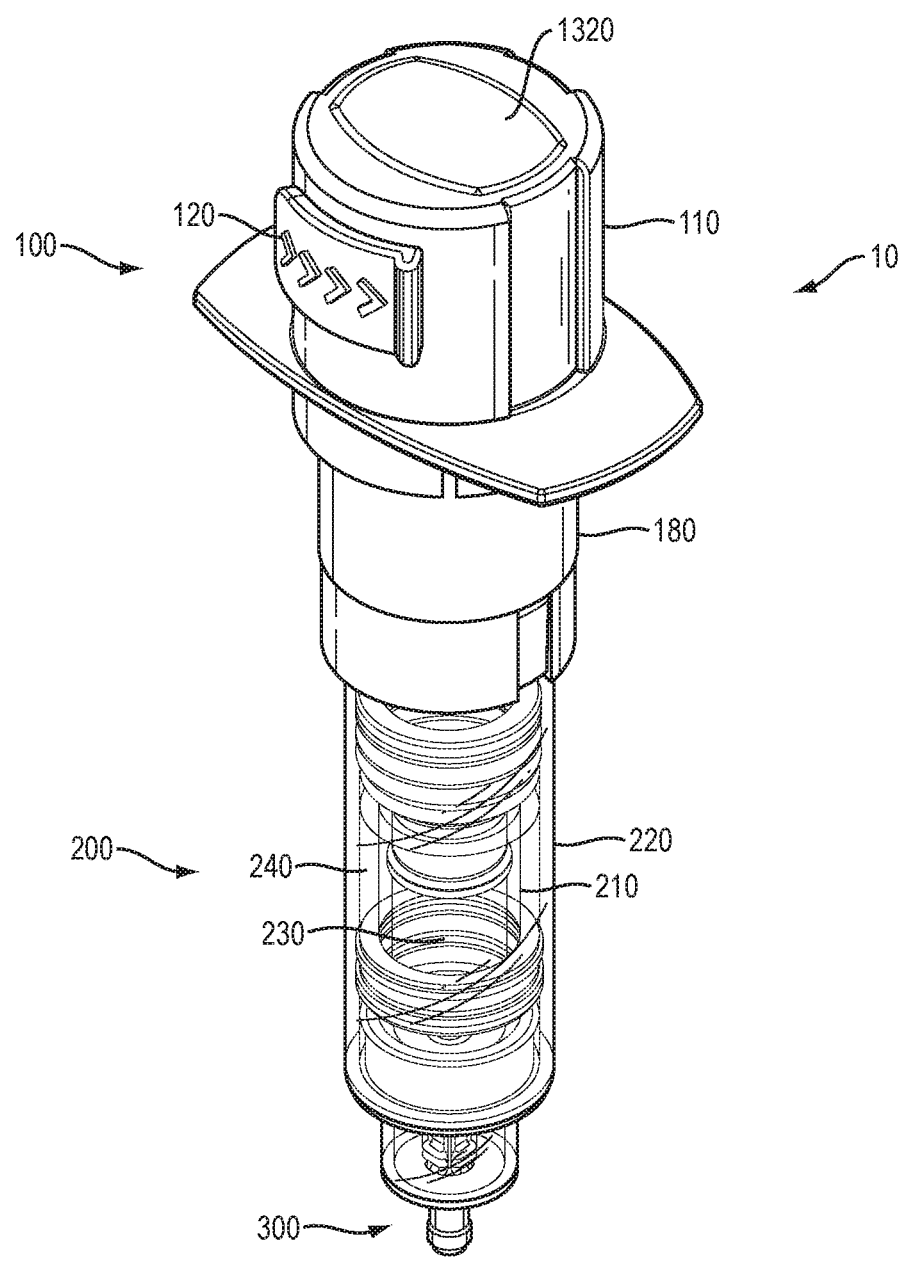
FIG. 1 shows an isometric view of an embodiment of an automatic mixing syringe comprising an actuating device coupled to a mixing device, according to one embodiment of the present invention.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. All statements as to the date or representation as to the contents of these documents are based on the information available to the applicants and does not constitute any admission as to the correctness of the dates or contents of these documents.

As used herein and in the claims, the singular forms include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where otherwise indicated, all numbers expressing quantities of ingredients or reaction conditions used herein should be understood as modified in all instances by the term "about."

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

The present embodiments provide for mixing syringes which generally comprise at least a first chamber for containing a first substance and a second chamber for containing a second substance, such that seals within the syringe are configured for maintaining the substances separately in their respective chambers until such time as it is desired by a user to mix the components within the syringe by manipulating the seals to provide fluid communication between the chambers.

References to "pharmaceutical agent," "pharmaceutically active," "pharmaceutical," "drug," "medicament" "active agent," "active drug" and the like, refer in a general sense to substances useful in the medical and scientific arts as suitable for delivery via a syringe, including, for example, drugs, biologics, diagnostic agents (e.g, dyes or contrast agents) or other substances used for therapeutic, diagnostic, or preventative (e.g., vaccines), or research purposes. "Inactive" substances refer to carriers, excipients, diluents, and the like, which are well-known in the art, although such substances may have beneficial function in the mixed injectable, such as, for example, adjuvants, isotonic or buffering agents.

"Fluid" refers primarily to liquids, but can also include suspensions of solids dispersed in liquids (dispersions, suspensions, colloidal mixtures), emulsions, liposomal compositions, and gasses dissolved in or otherwise present together within liquids inside the fluid-containing portions of syringes.

As used herein to describe the relative positions of the components of the present embodiments, the terms "axial" or "axially" refer generally to a longitudinal axis "A" of the barrel of the syringe and plunger in which or around components are positioned, although not necessarily symmetrically there-around. The term "radial" refers generally to a direction perpendicular to axis A. The terms "proximal," "rear," "rearward," "back," or "backward" refer generally to an axial direction in the direction "P." The terms "distal," "front," "frontward," "depressed," or "forward" refer generally to an axial direction in the direction "D," toward the dispensing end of the syringe.

As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP).

The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, or plasticizers, etc., and that can be formed or molded under heat and pressure. As used herein, the term "plastic" can include pharmaceutical grade non-reactive polymers or elastomers that are approved for use in applications where they are in direct contact with therapeutic substances, such that the plastics do not interact with the substances contacting the plastic and are not readily susceptible to leaching or gas migration under ambient temperature and pressure.

The term "elastomer," "elastomeric" or "elastomeric material" refers primarily to cross-linked thermosetting rubbery polymers that are more easily deformable than resilient plastics, are approved for use with pharmaceutical grade substances, and are not readily susceptible to leaching or gas migration under ambient temperature and pressure.

According to various aspects and embodiments described herein, reference is made to a "biasing member". It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The present invention provides an actuating device with an integrated plunger which may be mounted or otherwise connected to a dual chamber mixing device for storing, transporting, mixing, and injecting a mixed drug substance to a patient. The actuating device may be incorporated as part of an automatic mixing device and/or syringe, or removably attached to a mixing device to produce an automatic mixing syringe. In one or more of these embodiments, the actuating device and/or plunger thereof may be utilized to facilitate moving, piercing, or removal of a membrane at the proximal end of the mixing device. The membrane, as is described further herein, may be a sterile barrier utilized to maintain container integrity of the mixing device prior to operation of the device. Accordingly, the novel actuating devices of the present invention aid in maintenance of the sterility of the mixing device, and at least partial moving, piercing, or removal of the membrane prior to operation of the device and/or syringe for drug injection. The distal end of the barrel may have a needle, cannula, or other conduit for fluid transfer to a user, to an intravenous (IV) line, fluid tube, or container, or the like. In at least one embodiment, the distal end of the barrel has a luer type connection, such as a luer lock connection, for connection of the barrel to a drug container, needle, or IV line.

In at least one embodiment, the syringe has a connection aspect for connection to a needleless access device (NLAD), such as an IV line or to a needle assembly. The connection aspect may be pre-formed as a distal portion of the syringe barrel housing. Alternatively, the syringe barrel may be a substantially straight barrel to which a connection adapter is mounted. An adapter mountable to a syringe barrel may have a luer connection portion and a barrel-engaging portion and a fluid aperture therethrough. The adapter facilitates mounting a luer assembly to the barrel. The luer assembly may be a tip cap having a corresponding female luer fitment for connection to the male luer fitment of the luer connection portion of the adapter. The luer assembly may alternatively be a luer needle assembly having a needle body, cannula, and a needle tip having a corresponding female luer fitment for connection to the male luer fitment of the luer connection portion of the adapter. The term male and female may be used interchangeably to describe corresponding components or aspects thereof. The adapter and syringe further comprise an immobile, compressible needle seal. The needle seal is adjacent to or engageable with the barrel-engaging portion of the adapter. The needle seal sits within the interior of the barrel and/or adapter and has a fluid pass-through preferably axially located for the passage of fluid.

In some embodiments, the outer and inner chambers can be prefilled to contain one or more mixing substances, i.e., outer and inner mixing substances, which may each be a powder, solid, liquid, suspension, gas, or mixtures of these substances. For example, the outer mixing substance locatable in the outer chamber may be a fluid that comprises a pharmaceutically active fluid or a pharmaceutically inactive fluid, such as a diluent. The inner mixing substance locatable in the inner chamber may be a fluid that comprises a pharmaceutically active fluid or a pharmaceutically inactive fluid, such as a diluent. Alternatively, for example, the inner substance locatable in the inner chamber may comprise a pharmaceutically active solid or an inactive solid excipient. As is well understood in the art, a pharmaceutically active component may be mixed with suitable excipients in its respective mutable chamber in the prefilled syringe. For example, a powdered drug is often lyophilized with salts, sugars, or polyols, such as mannitol or lactose; a liquid drug is often formulated in ethanol, buffers, or non-aqueous or aqueous solvents. In a preferred embodiment, the inner mixing substance is a pharmaceutically active solid and the outer mixing substance is a pharmaceutically inactive diluent.

While the embodiments described herein may describe certain components of the automatic mixing syringe, actuating device and mixing device as separate components, these may readily be manufactured as integrally formed or unitary components. Similarly, while the embodiments described herein may describe certain components of the automatic mixing syringe, actuating device and mixing device as integrally formed or unitary components, these may readily be manufactured as separate components that are subsequently assembled before use.

Figure 3:
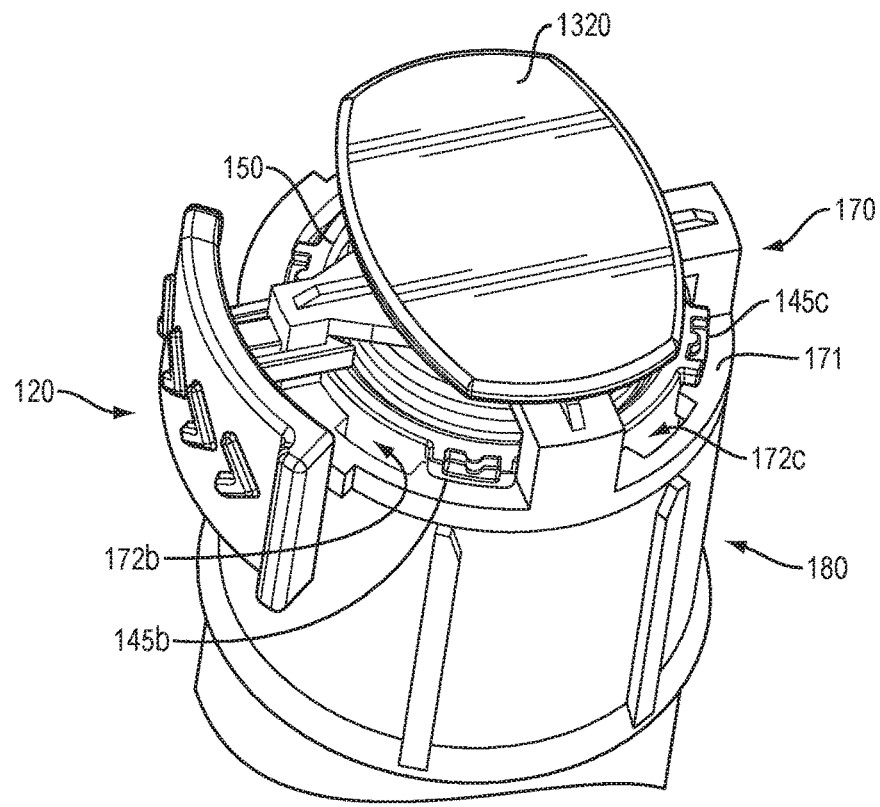
FIG. 3 shows an isometric view of the actuating device shown in FIG. 1 with the upper housing hidden.
Figure 7:
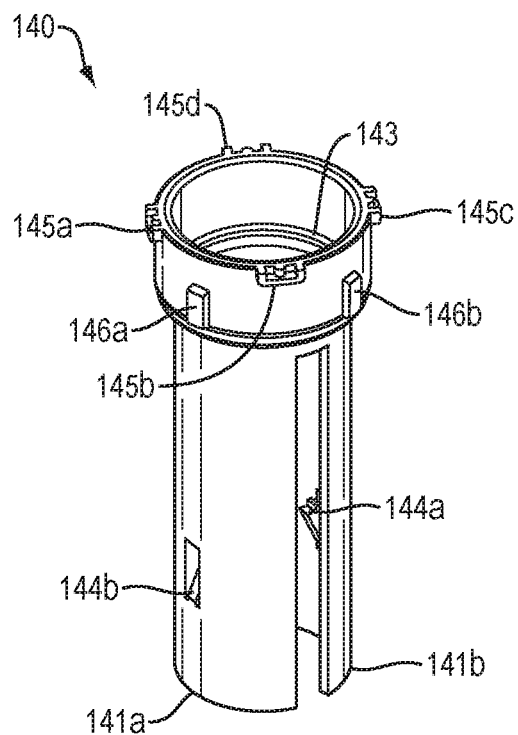
FIG. 7 shows an isometric view of a mixing plunger sleeve according to at least one embodiment of the present invention.
Figure 8:
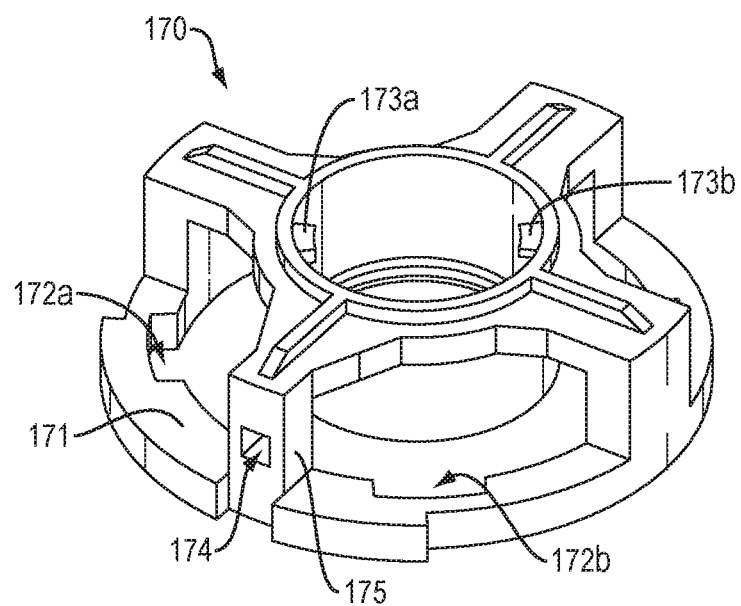
FIG. 8 shows an isometric view of a lockout ring according to at least one embodiment of the present invention.
Figure 9:
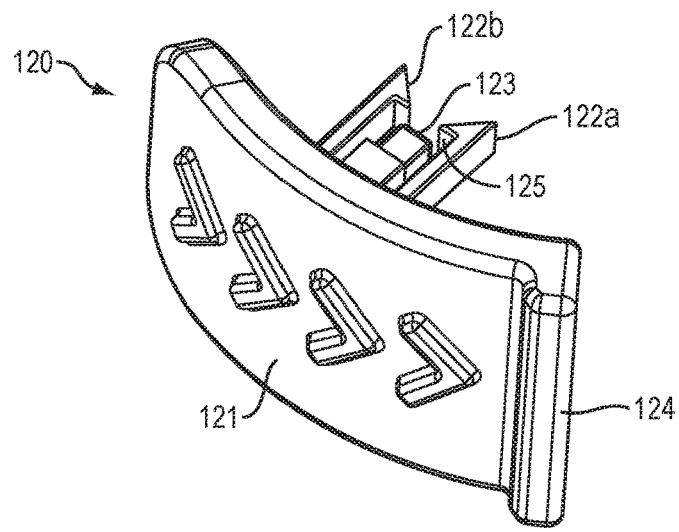
FIG. 9 shows an isometric view of a trigger member according to at least one embodiment of the present invention.
Figure 14A:
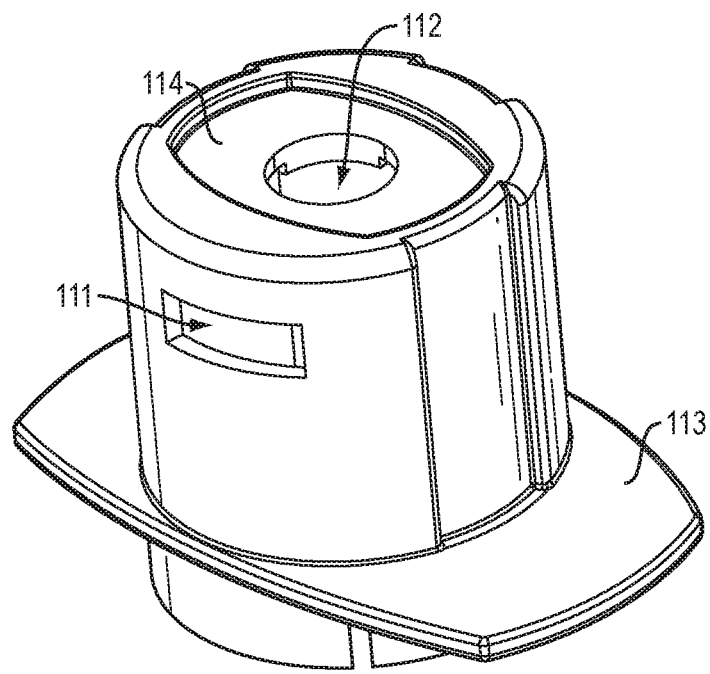
FIG. 14A shows an isometric view of an upper housing according to at least one embodiment of the present invention.

Referring to FIG. 1, automatic mixing syringe 10 comprises actuating device 100, mixing device 200 and end fitment 300. Mixing device 200 has dual concentric inner and outer barrels 210, 220. Inner chamber 230 is located within inner barrel 210 and outer chamber 240 is located between outer barrel 220 and inner barrel 210. Reference is also made to FIGS. 2A and 2B which show an exploded view and a cross-sectional exploded view of an embodiment of actuating device 100 and FIGS. 3-5 which show detail views of the assembled actuating device 100. Upper housing 110, shown in more detail in FIGS. 14A and B, further comprises first opening 111, second opening 112, flange 113, recess 114, and protrusions 115A,B (115B not shown). A delivery plunger 1300 includes button 1320, inner sleeve 1330, intermediate sleeve 1340, outer sleeve 1350, seal-engaging member 1360, and plunger biasing member 1370. One or more of the components of delivery plunger 1300 are configured to pass through an opening, such as second opening 112 of upper housing 110 such that it may axially translate, as will be described in more detail hereinafter. Trigger member 120, as shown in FIG. 9, may further include user interface 121, locking prongs 122A,B, and protrusion 123. Mixing plunger 140, as shown in FIG. 7, comprises sleeve members 141A, B, plateau 143, flex arms 144A, protrusions 145A-D, and bosses 146A-D (C and D not shown). FIG. 8 shows lockout ring 170 which further includes flange 171, apertures 172A-D (C and D not shown) in flange 171, protrusions 173A,B, opening 174, and post 175. Mixing biasing member 150 in this embodiment is a spring which is initially compressed (i.e., energized) prior to activation of the actuating device 100. Lower housing 180 is configured to engage outer barrel 220 such as, for example, at outer barrel extension 225. Referring again to FIG. 1, it will be appreciated that while plunger 1300 is capable of axial translation within inner chamber 230 of the mixing device 200 and mixing plunger 140 is capable of axial travel within outer chamber 240 of mixing device 200, this is initially prevented or impeded until rotation of the lockout ring 170, as will be described hereinafter. As shown in FIG. 3 (upper housing 110 not shown for clarity), at least a portion of trigger member 120 passes through first opening 111 of upper housing 110 and is rotatably engaged with lockout ring 170 such that rotation of trigger member 120 with respect to upper housing 110 is transferred to lockout ring 170. FIG. 3 shows a releasable locking arrangement between the mixing plunger 140 and lockout ring 170. The mixing plunger 140 is initially engaged with the lockout ring 170 through releasably engageable interaction between protrusions 145A-D and flange 171. The mixing biasing member 150 is initially retained in an energized state between the lockout ring 170 and the mixing plunger sleeve 140. In at least one embodiment, the mixing biasing member 150 is initially retained between lockout ring 170 and plateau 143 of the mixing plunger 140.

Figure 14B:
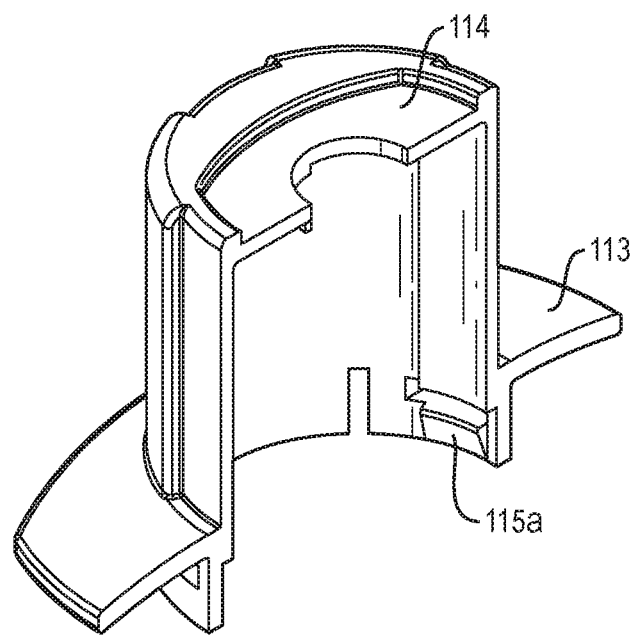
FIG. 14B shows a cross-sectional isometric view of an upper housing according to at least one embodiment of the present invention.

Lower housing 180 may be configured to engage an aspect of outer barrel 220 such as, for example, outer barrel extension 225. Locking extensions 181 of lower housing 180 may be configured to engage recesses 226 of outer barrel extension 225. Alternatively, lower housing 180 may be configured to engage outer barrel 220 or outer barrel extension 225 in any number of ways including: press-fit, thread engagement, bonding, etc. The engagement of lower housing 180 with outer barrel 220 may be substantially permanent such that actuating device 100 cannot be removed from mixing device 200 or may be releasable such that actuating device 100 may be removed from mixing device 200. Removing of actuating device 100 may be preferable to limit the waste required to be disposed of in a sharps container. Lower housing 180 may further include guide tracks 182 which may engage bosses 146 of mixing plunger 140 to limit rotation of mixing plunger 140 with respect to lower housing 180. Lower housing 180 may further include protrusions 183 which are configured to engage upper housing 110 such that upper housing 110 may be mounted to lower housing 180 with flanges 115A, B shown in FIG. 14B.

Sleeve members 141A, B are configured to connect to, bear against or contact proximal seal 250 residing within outer chamber 240 between the outer barrel 220 and the inner barrel 210 of the mixing device 200. Distal seal 260 is also located in outer chamber 240 between the outer barrel 220 and the inner barrel 210 of the mixing device 200, the function of which will be described in more detail hereinafter. Mixing device 200 further comprises vent cap 270 mounted thereto. In this embodiment, distal seal 260 is located proximal to or in sealing engagement with apertures 211 in inner barrel 210 which form respective fluid paths between the outer chamber 240 and the inner chamber 230. Vent chamber 280 is located distal to distal seal 260. As will be described in more detail hereinafter, manipulation and operation of the actuating device 100 facilitates the mixing of a first substance contained in the outer chamber 240 with a second substance contained in the inner chamber 230. The mixed substance may then be injected through the end fitment 300 by axial translation of the delivery plunger 1300, for drug delivery into a patient.

Trigger member 120 is shown in detail in FIG. 9. User interface 121 of trigger member 120 may be configured with a textured surface or with an embossed surface which allows it to be easily displaced by the user. Stop 124 may further be provided such that the user may rest their finger, thumb, or palm against the stop in order to activate mixing. The trigger member is preferably configured to allow use by users with decreased dexterity. Locking prongs 122A,B and protrusion 123 pass through first opening 111 of upper housing 110 and engage lockout ring 170. Prongs 122A,B may be configured to engage post 175 of lockout ring 170 such that trigger member 120 may not be removed by the user. Prongs 122A,B may be configured such that, during installation, the prongs flex outward in response to contact with post 175. Once face 125 has been translated past post 175 prongs 122 A,B may flex toward their natural positions, thereby locking the trigger member 120 to lockout ring 170. Further, during installation, protrusion 123 may engage opening 174 of lockout ring 170. This engagement may couple rotation of trigger member 120 and lockout ring 170 such that rotation of trigger member 120 is transferred to lockout ring 170. One or more safety features may be used to prevent unintentional or inadvertent rotation of trigger member 120. This may include a safety stop, engaged with first opening 111 of upper housing 110 that must be removed by the user prior to rotation of trigger member 120.

Figure 6A:
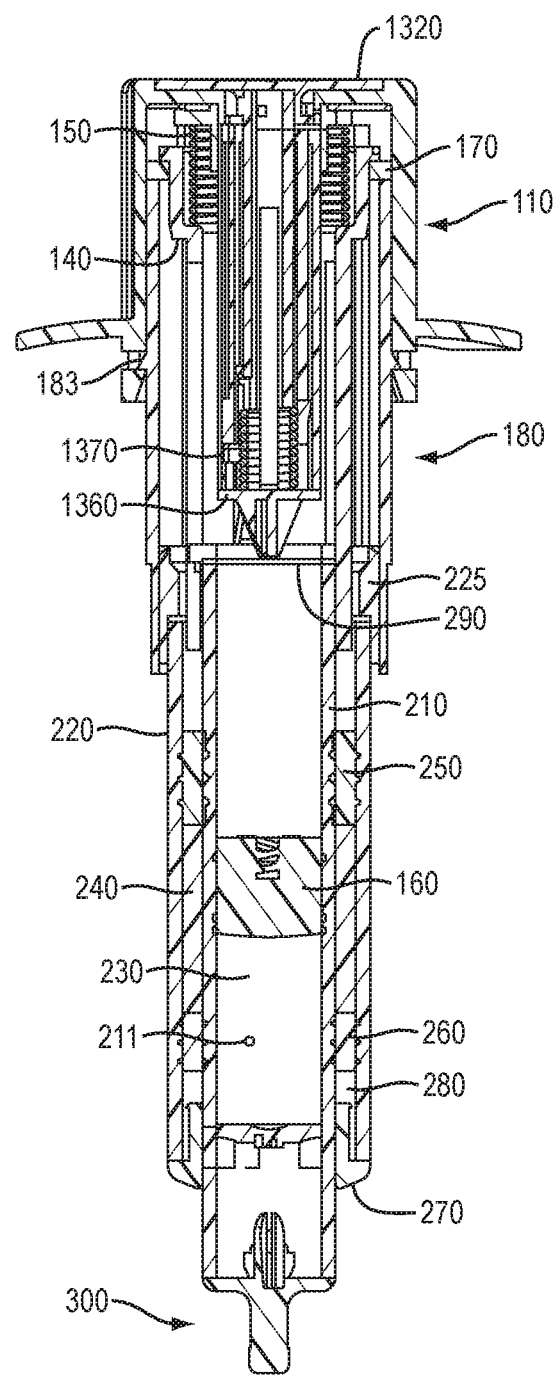
FIG. 6A shows a cross-sectional view of the embodiment shown in FIG. 1 with the actuating device having a locked trigger member.
Figure 10A:
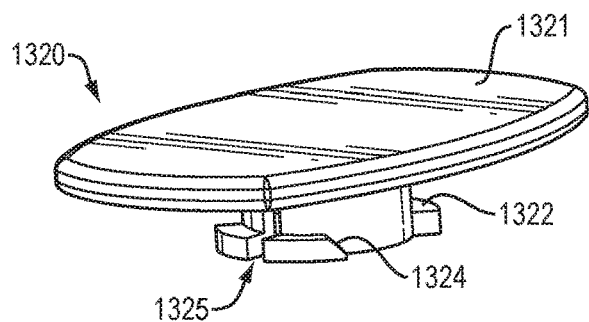
FIG. 10A shows an isometric view of a cap according to at least one embodiment of the present invention.
Figure 10B:
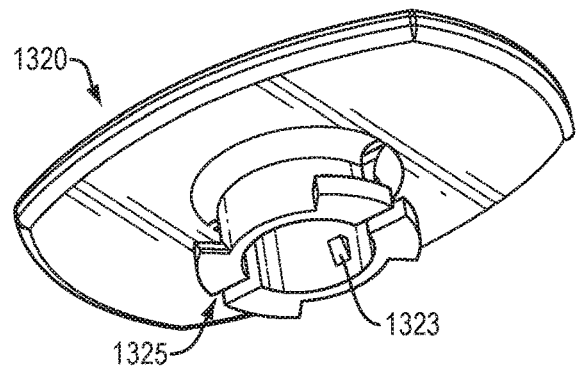
FIG. 10B shows an isometric view of a cap according to at least one embodiment of the present invention.

Cap 1320, as shown in FIGS. 10A and 10B, includes top 1321, flange 1322, and protrusion 1323. Top 1321 is configured to be depressed by the user to initiate and/or actuate delivery of the mixed contents of mixing device 200. Top 1321 may be configured to be at least partially disposed within recess 114 of upper housing 110 in an initial configuration as shown in FIG. 6A. Cap 1320 may additionally be at least partially disposed in recess 114 at completion of drug delivery as shown in FIG. 6D. Flange 1322 is configured to engage protrusion 173 of lockout ring 170 such that in an initial configuration this engagement prevents axial translation of cap 1320 with respect to lockout ring 170. Flange 1322 may further include ramped surface 1324 which may ease engagement and/or disengagement of flange 1322 with protrusion 173. Projection 1323 of cap 1320 may be engagable with window 1331 of inner sleeve 1330. This engagement may prevent axial displacement, in the proximal direction, of cap 1320 with respect to inner sleeve 1330. Axial displacement of cap 1320 in the distal direction is limited by interaction of cap 1320 with the proximal end of inner sleeve 1330. Slots 1325 of cap 1320 are configured to engage with protrusions 1332 of inner sleeve 1330. This engagement limits rotation of cap 1320 with respect to inner sleeve 1330.

Figure 11:
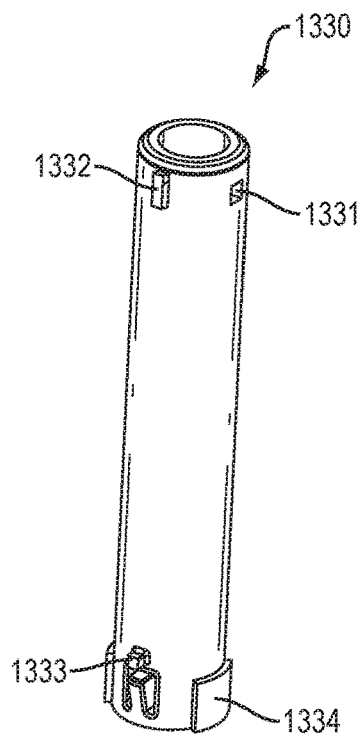
FIG. 11 shows an isometric view of an inner sleeve according to at least one embodiment of the present invention.
Figure 12A:
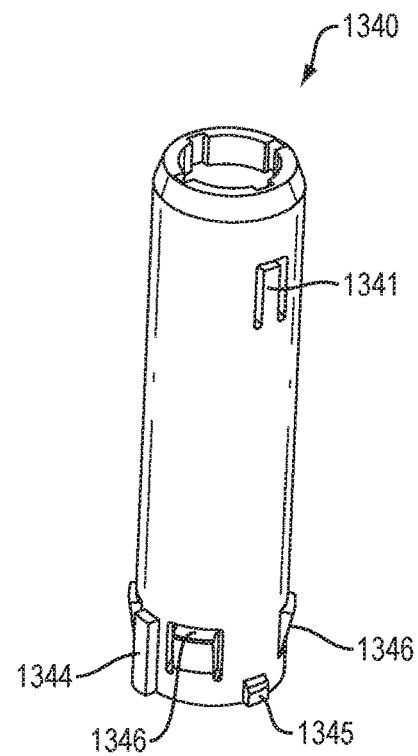
FIG. 12A shows an isometric view of an intermediate sleeve according to at least one embodiment of the present invention.
Figure 12B:
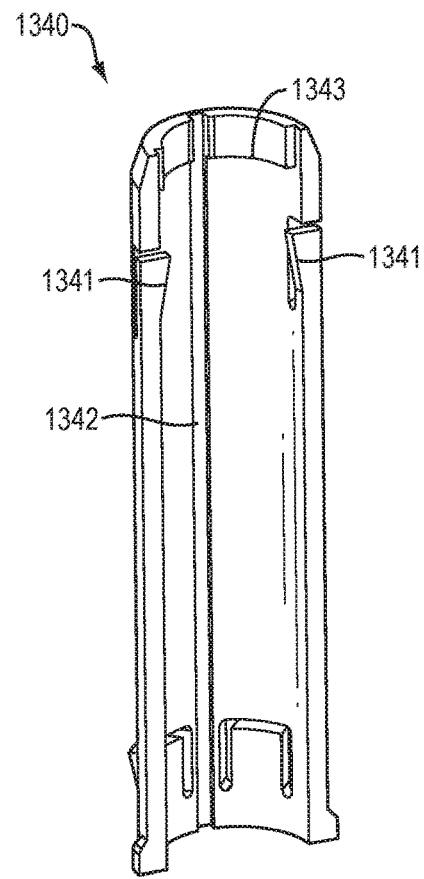
FIG. 12B shows a cross-sectional isometric view of an intermediate sleeve according to at least one embodiment of the present invention.

Inner sleeve 1330, as shown in FIG. 11, further includes projection 1333 which is configured to engage slots 1342 of intermediate sleeve 1340 (shown in FIGS. 12A and 12B). Engagement of projection 1333 with slots 1342 limits rotation of inner sleeve 1330 with respect to intermediate sleeve 1340. Inner sleeve 1330 may also include bosses 1334 which, upon activation of expansion of plunger 1300, limit axial displacement of inner sleeve 1330 with respect to intermediate sleeve 1340. During expansion of plunger 1300 bosses 1334 come into contact with ledge 1343 of intermediate sleeve 1340, thus limiting translation of inner sleeve 1330 in the proximal direction with respect to intermediate sleeve 1340. After expansion of plunger 1300, translation of inner sleeve 1330 in the distal direction with respect to intermediate sleeve 1340 is limited by contact between the distal end of inner sleeve 1330 and lockouts 1341 of intermediate sleeve 1340. Hence, after expansion of plunger 1300 inner sleeve 1330 is substantially fixed in position with respect to intermediate sleeve 1340.

Intermediate sleeve 1340 further includes projection 1344 which is configured to engage slot 1352 of outer sleeve 1350 and thereby limit rotation of intermediate sleeve 1340 with respect to outer sleeve 1350. Boss 1345 is configured to interact with lockout 1351 of outer sleeve 1350. During expansion of plunger 1330, interference between boss 1345 and lockout 1352 causes lockout 1351 to be displaced radially outward such that boss 1345 may translate in the proximal direction, past lockout 1351. After boss 1345 has translated past lockout 1351, lockout 1351 may displace radially inward toward its natural position. After this translation, interaction between boss 1345 and lockout 1351 limits axial translation of intermediate sleeve 1340, in the distal direction, with respect to outer sleeve 1350. Interaction of extensions 1346 with ledge 1354 of outer sleeve 1350 limits translation of intermediate sleeve 1340, in the proximal direction, with respect to outer sleeve 1350. Hence, after expansion of plunger 1300 intermediate sleeve 1330 is substantially fixed in axial position with respect to outer sleeve 1350.

Figure 13:
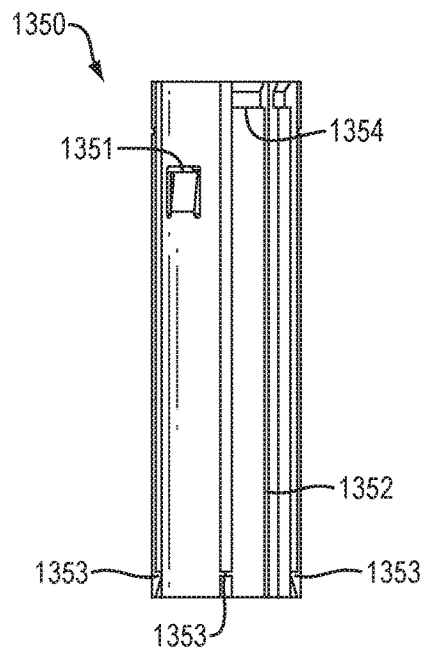
FIG. 13 shows a cross-sectional view of an outer sleeve according to at least one embodiment of the present invention.

Outer sleeve 1350, as shown in FIG. 13, further includes distal ledge 1353 which is configured to engage locking prongs 1363 of seal engaging member 1360. This engagement limits translation of outer sleeve 1350 with respect to seal engaging member 1360 in the proximal direction and may also limit rotation. Translation of outer sleeve 1350 with respect to seal engaging member 1360 in the distal direction is limited by contact between the distal face of outer sleeve 1350 and seal engaging member 1360.

Although the embodiments of the expandable delivery plunger shown and described herein include three sleeves, any number of sleeves can be used. The expanding plunger allows for a compact device for shipping and packaging and may further reduce the risk of unintentional depression of the plunger.

Figure 4:
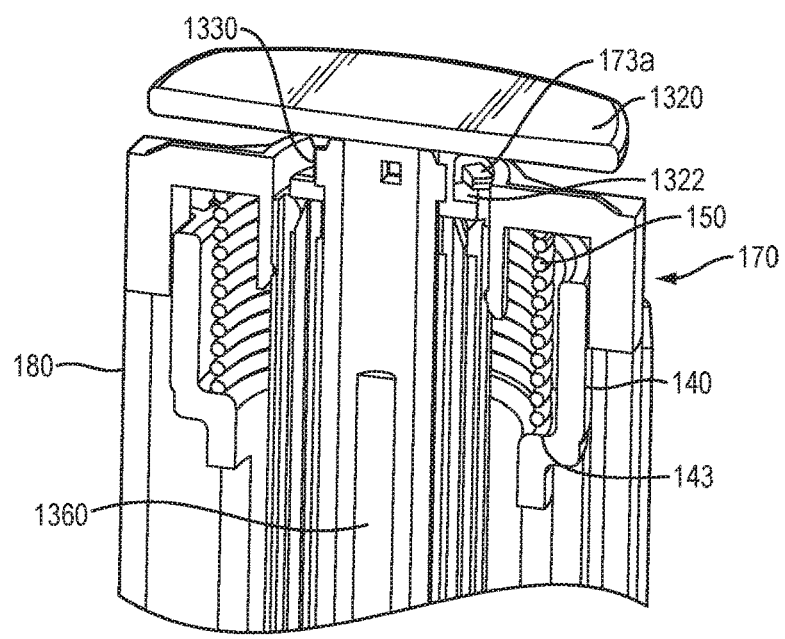
FIG. 4 shows a detail cross-sectional isometric view of a proximal end of the actuating device shown in FIG. 1 with the upper housing hidden.
Figure 5:
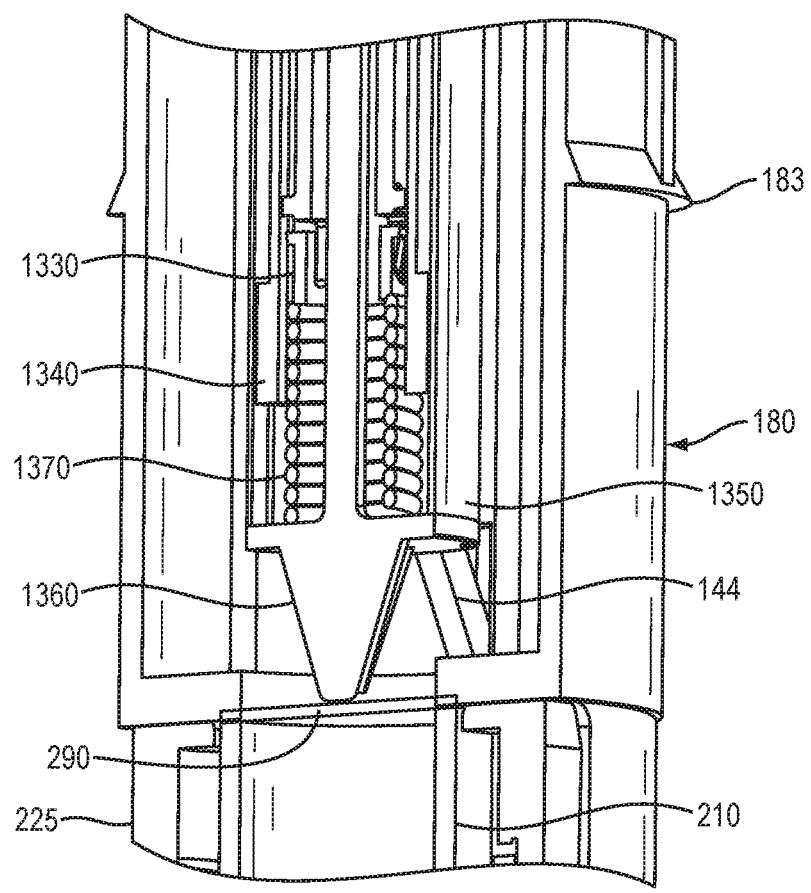
FIG. 5 shows a detail cross-sectional isometric view of a distal end of the actuating device shown in FIG. 1.

FIGS. 3 and 4 show an isometric view and a cross-sectional isometric view of the embodiment shown in FIG. 1 and FIG. 2, in an initial locked configuration such as may be utilized for storage or transportation. Plunger 1300 is incapable of axial translation within inner chamber 230 of the mixing device 200 and mixing plunger 140 is incapable of axial travel within outer chamber 240 of mixing device 200 until rotation of lockout ring 170. FIG. 3 shows the engagement of protrusions 145 of mixing plunger 140 and lockout ring 170 which prevents axial translation of mixing plunger 140. FIG. 4 shows the engagement of flange 1322 of cap 1320 with protrusion 173 of lockout ring 170 which prevents axial translation of cap 1320. The actuating device 100 may be pre-formed with the mixing device 200 to produce an automatic mixing syringe 10, or the actuating device 100 and mixing device 200 may be separate structures that are connected or otherwise mounted together. In the latter embodiment, the mixing device 200 may comprise a mount upon which the housing 180 of the actuating device 100 may be connected. In at least one embodiment, the mount is located at the proximal end P of the outer barrel 220 of the mixing device 200. As described above, a mixing plunger 140 of the actuating device 100 is configured to at least partially reside and axially translate within outer chamber 240 of the mixing device 200. Axial translation of the mixing plunger sleeve 140 causes axial translation of the proximal seal 250 and thereby causes fluid transfer from the outer chamber 240 to the inner chamber 230 of the mixing device 200, as described further herein. The sleeve 140 is caused to axially translate by operation of a trigger member 120. As shown in FIG. 5, in the initial locked state of actuating device 100 seal engaging member 1360 bears against flex arms 144A,B (144B not shown) of mixing plunger sleeve 140 to prevent translation in the distal direction of seal engaging member 1360 and hence decompression or de-energizing of plunger biasing member 1340.

Figure 6B:
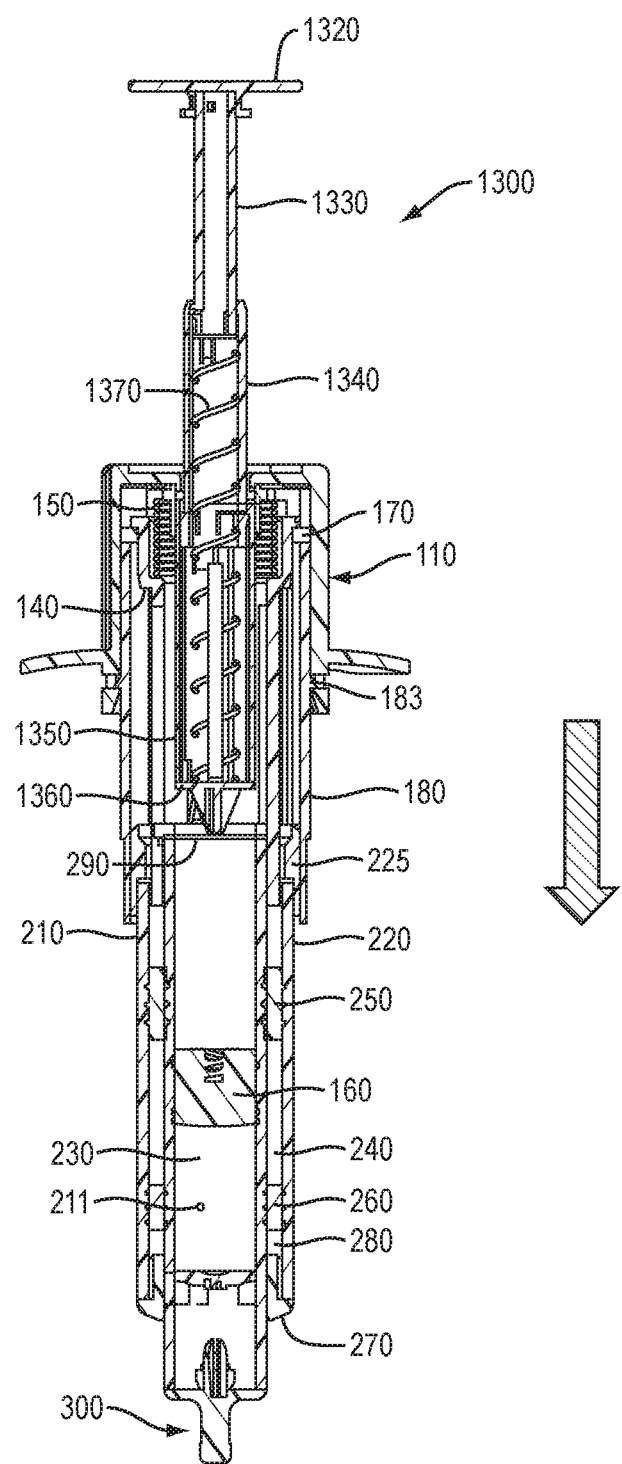
FIG. 6B shows a cross-sectional view of the embodiment shown in FIG. 1 after the expansion of the delivery plunger has been activated by the actuating device.
Figure 6C:
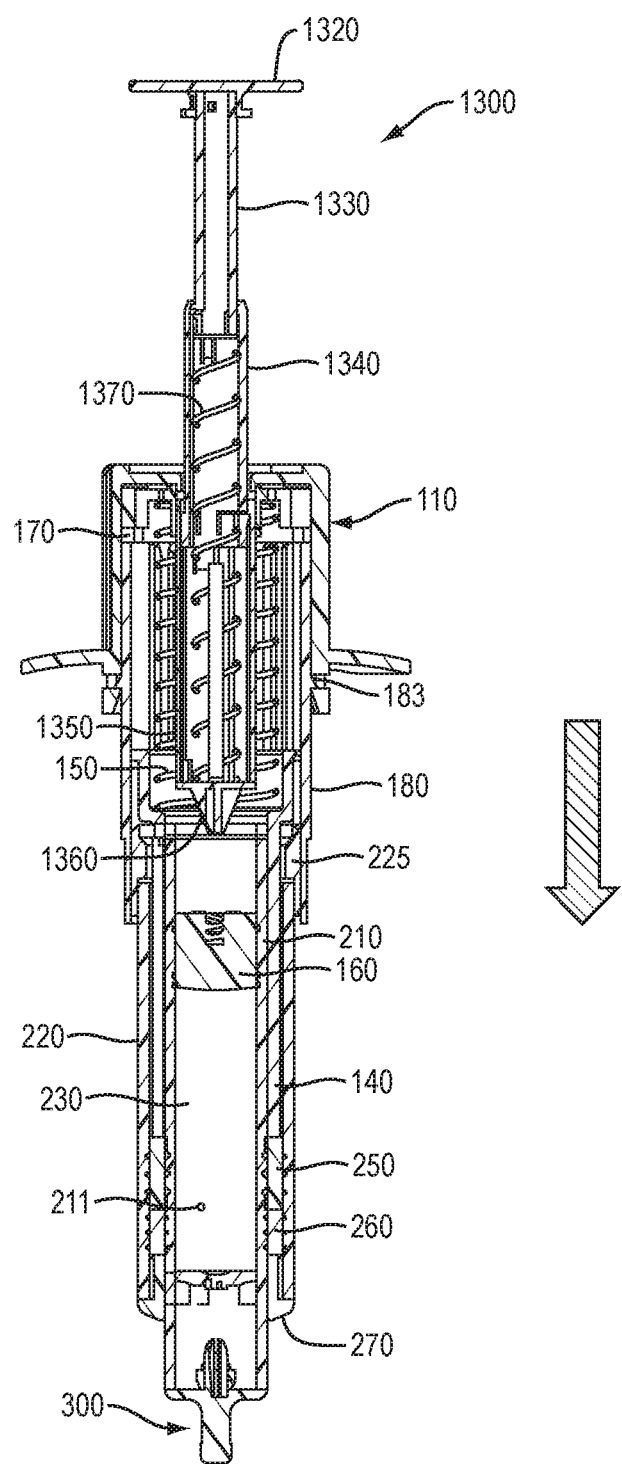
FIG. 6C shows a cross-sectional view of the embodiment shown in FIG. 1 after the mixing plunger has been activated by the actuating device.
Figure 6D:
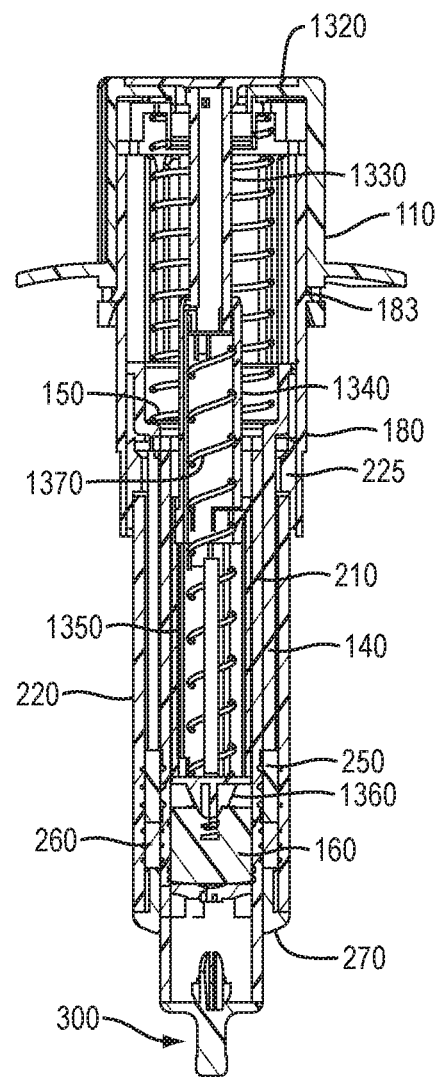
FIG. 6D shows a cross-sectional view of the embodiment shown in FIG. 1 after delivery of the contents of the mixing syringe.

FIGS. 6A-D show a cross-sectional side view of the embodiment shown in FIG. 1 in various stages of operation. In the embodiment shown, the trigger member 120 (not shown in FIGS. 6A-D) may be rotated anticlockwise by a user to activate the actuating device 100. In the initial configuration, shown in FIG. 6A, extension biasing member 1370 is held in a compressed or energized state between seal engaging member 1360 and the distal end of inner sleeve 1330. Alternatively, extension biasing member 1360 may be located between seal engaging member 1360 and cap 1320. It is anticipated that the actuating device 100 may alternatively be configured such that rotation of trigger member 120 in the clockwise direction may allow the user to activate the actuation device 100. Upon rotation of trigger member 120 lockout ring 170 is rotated such that protrusions 173A,B are disengaged from flange 1322 of button 1320. In this position, extension biasing member 1370 is able to decompress or de-energize and cause delivery plunger 1300 to expand as shown in FIG. 6B. Expansion of delivery plunger 1300 occurs by translation of inner sleeve 1330 and intermediate sleeve 1340 with respect to one another and with respect to outer sleeve 1350. Upon completion of translation the sleeves are substantially fixed in axial position with respect to one another as described above. Continued rotation of trigger member 120 may also disengage protrusions 145A-D of mixing plunger 140 from flange 171 of lockout ring 170 such that protrusions 145A-D are aligned with apertures 172A-D. In this position mixing biasing member 150 is able to decompress or de-energize and hence cause translation of mixing plunger sleeve 140 with respect to actuation mechanism 100 as shown in FIG. 6C. Such axial translation of the mixing plunger 140 causes the sleeve members 141A, B to contact and axially translate the proximal seal 250 of the mixing device 100. Therefore, distal movement of the mixing plunger sleeve 140 of the actuating device 100 causes movement of the proximal seal 250 to which the sleeve members 141A,B are engaged or bear against. A first mixing substance may be contained in outer chamber 240 between the outer barrel 220 and the inner barrel 210 and between the proximal seal 250 and the distal seal 260 in the outer chamber 240. The distal seal 260 may initially be in a first position at least partially above (i.e., proximal to) one or more apertures 211 that are in the inner barrel 210 between the outer chamber 230 and the inner chamber 240. Movement of the mixing plunger sleeve 140 and the proximal seal 250 is relayed to the first mixing substance in the outer chamber 240 and, similarly, to the distal seal 260. In at least one embodiment, the movement of the mixing plunger sleeve 140, the proximal seal 250 and, accordingly, the first mixing substance in the outer chamber 240 is relayed to the distal seal 260 by pneumatic and/or hydraulic pressure or force created in the first mixing substance by the motion of the proximal seal 250. Accordingly, axial movement of the mixing plunger sleeve 140 indirectly (i.e., without needing direct contact) facilitates axial movement of the distal seal 260 to a second position. Upon movement of the distal seal 260 to a second position (i.e., in the direction of the hatched arrow in FIGS. 6A and 6B), the first mixing substance contained in the outer chamber 240 may pass-through the one or more apertures 211 and into the inner chamber 230 of the inner barrel 210. Upon completion of mixing, the mixing plunger sleeve 140 may be restricted from movement in the proximal direction, for example by one or more lockout features interacting with an inner lip of the outer barrel 220 or outer barrel extension 225. The restriction of movement in the proximal direction may aid in ensuring that contents do not reenter the outer chamber 240 during delivery to the user.

The one or more fluid paths may comprise one or more apertures, holes, bores, ports, pass-throughs or conduits. These may be of any suitable shape, configuration, arrangement and/or number. Preferably, the fluid path comprises a plurality of apertures. The apertures may be radial bores (i.e., normal to the axis of the barrel), angular bores (i.e., at an angle to axis of the barrel), helical (e.g., an angular and radial path as it traverses the thickness of the barrel wall), or any number of other configurations. The number and placement of the apertures, in locational spacing and arrangement, may also be adjusted for the desired mixing characteristics. As such, these parameters of the apertures may be configured to promote the desired mixing, dilution, and other fluid flow characteristics of the mixing syringe. Suitably, the mixing device may comprise one or more components described in International Publication WO2013/020170, which is incorporated by reference in its entirety for all purposes.

Figure 15A:
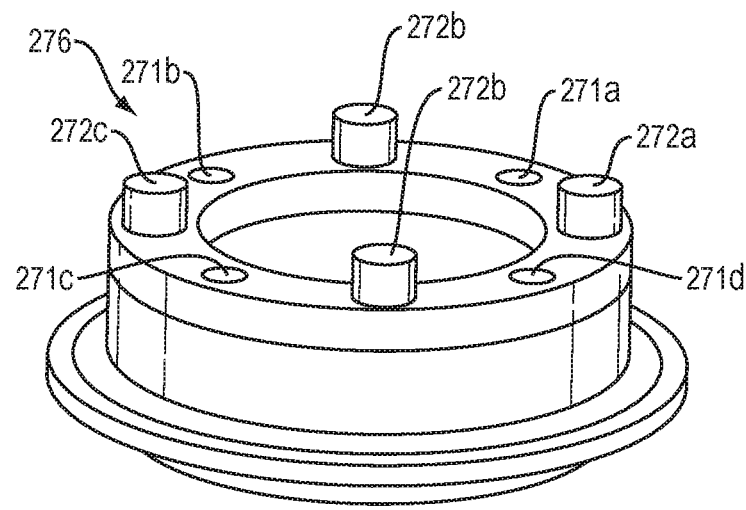
FIG. 15A shows an embodiment of a vent cap.
Figure 15B:
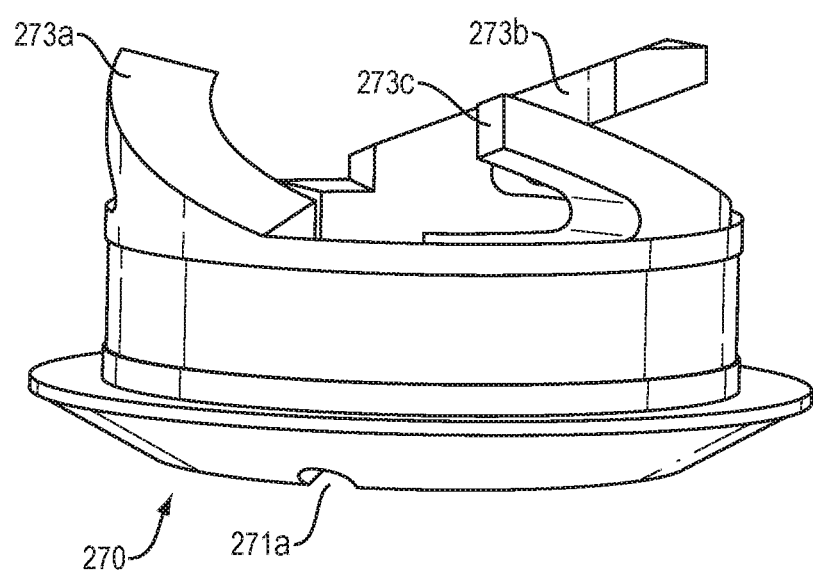
FIG. 15B shows another embodiment of a vent cap.

In some embodiments, vent cap 270 may be essentially as described in International Publication WO2013/020170. Vent cap 270 may optionally have "internal" vent cap features locatable within outer chamber 240 which facilitate the desired positioning of the distal seal 260 during operation of the mixing device 100. The "internal" vent cap features may be, for example, projections such as posts, prongs, flex arms, or the like which are configured to correctly position the distal seal 260 upon axial translation within the outer chamber 240, with reference to the one or more apertures 211, to enable substantially all of the first substance within the outer chamber 240 to be passed-through to the inner chamber. FIG. 15A shows an embodiment of the vent cap 270 having vents 271A, B, C, D and posts 272A, B, C, D, which would be internally located inside outer chamber 240. FIG. 15B shows an embodiment of the vent cap 270 having flex arms 273A, B, C which would be internally located inside outer chamber 240. The apertures 211 between the outer 240 and inner 230 chambers are desired to remain open to allow movement of the first substance until substantially all of the first substance is pushed out of the outer chamber 240 by the proximal mixing plunger seal 250. This may be achieved by the compressibility of the proximal seal 250 itself. Additionally or alternatively, the dimensions and the flexing capabilities of the internal vent cap features may be configured to align the distal seal 260 with the apertures 211 to ensure that substantially all of the first substance within the outer chamber 240 is able to be passed-through to the inner chamber 230. Accordingly, the distal seal 260 is permitted to float or self-adjust with reference to the apertures 211 so that the apertures 211 remain open until the proximal mixing plunger seal 250 contacts the distal seal 260 and substantially all of the first substance is pushed out of the outer chamber 240 into the inner chamber 230 by the proximal mixing plunger seal 250.

It will be appreciated that the vent chamber 280 between the distal seal 260 and vent cap 270 is never in contact with any substance(s) in mixing device 200, hence there is no need to maintain sterility in vent chamber 280. Vent chamber 280 may fill with air, which is displaced out of the annular space between outer barrel 220 and inner barrel 210 and between the vents 271 of the vent cap 270 and the distal seal 260 upon depression of proximal seal 250 and axial movement of distal seal 260 Furthermore, because distal seal 260 initially covers apertures 211 in inner barrel 210, sterility of the fluid path between outer chamber 240 and inner chamber 230 is maintained during use of mixing device 200. Only distal seal 260 is potentially in contact with any non-sterile portion of outer barrel 220 and inner barrel 210, as fluid is caused to flow from outer chamber 240 into inner chamber 230 without ever contacting the non-sterile portion.

It will also be appreciated that automatic mixing syringe 10 is a "closed system," meaning there is no venting of the fluid path other than by connection through end fitment 300 such as, for example, needle injection. Accordingly, delivery plunger seal 160 may axially move in inner chamber 230 in the proximal direction in response to the distal movement of sleeve 140. This is because distal movement of the sleeve 140 against proximal seal 250 forces liquid from outer chamber 240 into the inner chamber 230 and increases the pressure and/or fluid volume within inner chamber 230. With end fitment 300 in a closed configuration, there is no space for volume expansion other than to force delivery plunger seal 160 in the proximal direction within inner chamber 230. This is a desirable response as it provides visual and tactile indication to the user that the mixing has completed and that injection may be initiated.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

As described above, a sealing membrane 290 may initially reside at the proximal end of the mixing device 200, such as at the proximal end of the inner barrel 210, to cover the proximal end of the barrel(s) 210, 220 after assembly and filling with substance(s), but before connection to the actuating device 100. The sealing membrane 290 may be any of a variety of sterile fabrics and materials, such as TYVEK, used in the medical devices and pharmaceuticals industry. The sealing membrane 290 may be removed, pierced, or otherwise bypassed by operation of the actuating device 100 or automatically by the syringe user during operation. In one embodiment the sealing membrane 290 is configured to seal the proximal end of the inner barrel 210 and be removed by axial translation of the sleeve members 141A, B. Concurrently with this action, as previously described, proximal seal 250 is axially, slidably movable in outer chamber 240 of outer barrel 220 of mixing device 200 to thereby deliver the contents of the outer chamber 240 to the inner chamber 230 via one or more apertures 211 in the inner barrel 210. In the embodiment of FIG. 1, the sealing membrane 290 may be discoidal and located in the inner chamber 230 without extending or otherwise having a position located in the outer chamber 240 and contactable by mixing plunger sleeve 140. In this embodiment, the sealing membrane 290 is puncturable or pierceable by the delivery plunger 1300 and is not contacted by the mixing plunger 140. A seal engaging member 1360, as shown in the embodiment of FIG. 1, is configured for such a function by having, for example, a pointed distal tip to pierce the sealing membrane 290 and engage delivery plunger seal 160.

Delivery plunger 1300 is configured to contact delivery plunger seal 160 which is axially, slidably movable in inner chamber 230 of inner barrel 110 of mixing device 200 to thereby deliver the mixed contents of the inner chamber 230. Delivery plunger 130 may be coupled to delivery plunger seal 160 by way of screw-threaded engagement of complementary screw threads or by contact engagement as shown in the embodiment of FIG. 1. At this stage, automatic mixing syringe 10 is ready for delivery of its mixed substances. If end fitment 300 is a retractable needle assembly the rigid needle shield may be removed, the cannula of the retractable needle is inserted into a recipient and delivery plunger 1300 is depressed to deliver the mixed, fluid contents of inner chamber 230 to the recipient. Alternatively, end fitment 300 may be connected to an IV line or other NLAD for delivery to the patient. FIG. 6D shows mixing syringe 10 after delivery of the mixed contents. Standard medical practices, such as manual agitation of the automatic mixing syringe 10 to further facilitate mixing of the substances and/or priming the syringe to remove any residual air prior to injection, may be performed prior to injection of the fluid contents.

The actuating device 100 with integrated plunger 1300 described herein may be separately assembled from the remainder of the automatic mixing syringe 10. This may be desirable where, for example, a pharmaceutical company wishes to fill the syringe 10 with the drug substance(s) in their standard fill-finish lines, and seal and ship such filled components to a separate company for final assembly. Additionally, this may be desirable for shipping, transportation, or a number of other reasons. Furthermore, it may be desirable to have the actuating device 100 as a separable component from the mixing device 200 of the automatic mixing syringe 10 for safe and efficient disposal of the components separately (i.e., only the portions contaminated by use need to be disposed in a safety sharps container, while the remaining components may be disposed of separately).

In at least some embodiments translation of mixing plunger sleeve 140 within outer chamber 240 occurs prior to or substantially concurrently with the expansion of delivery plunger 1300. In this way, the risk of premature delivery of the contents of mixing syringe 10 is reduced.

Figure 16:
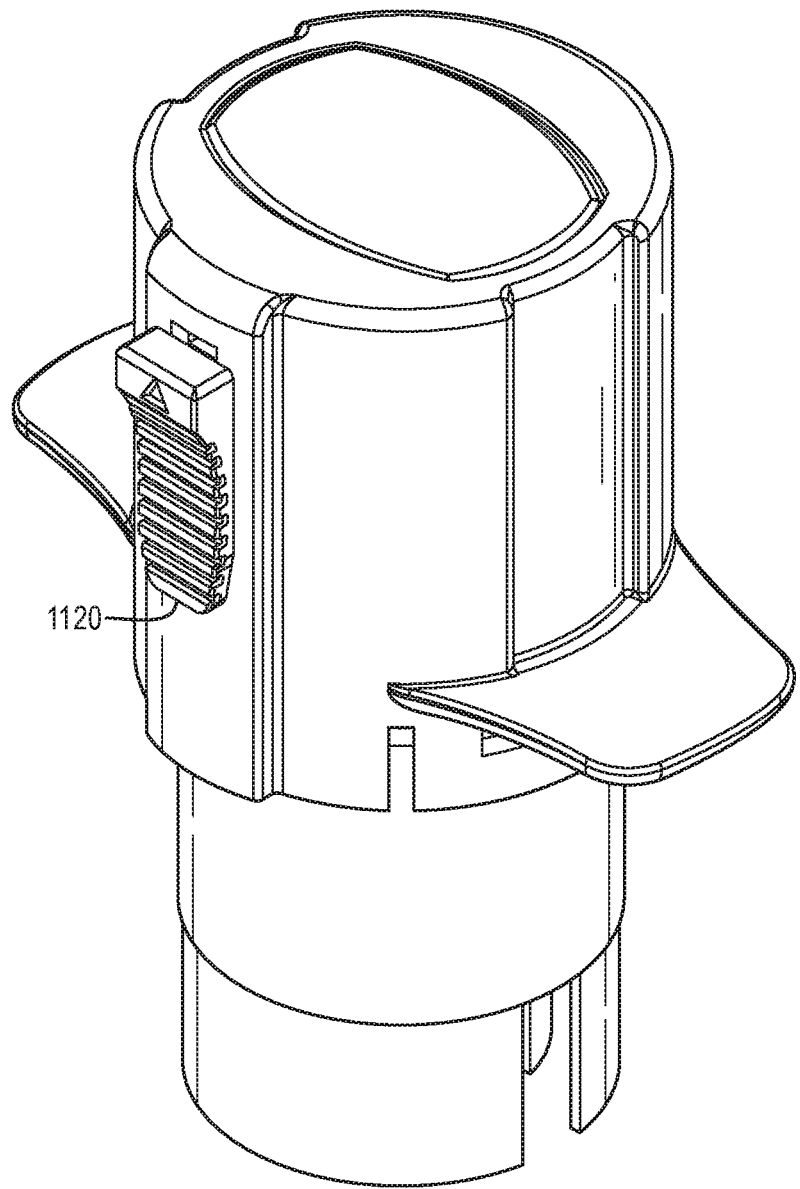
FIG. 16 shows an isometric view of an actuating device according to at least one embodiment of the present invention.
Figure 17:
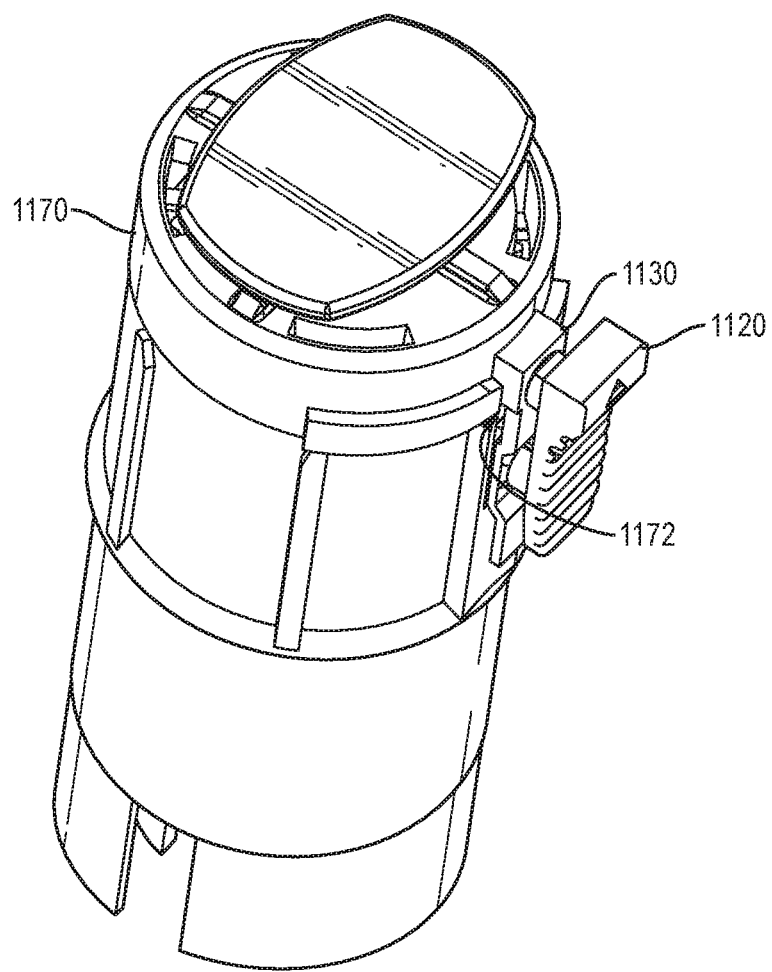
FIG. 17 shows an isometric view of an actuating device of at least one embodiment of the present invention with the upper housing hidden.
Figure 18:
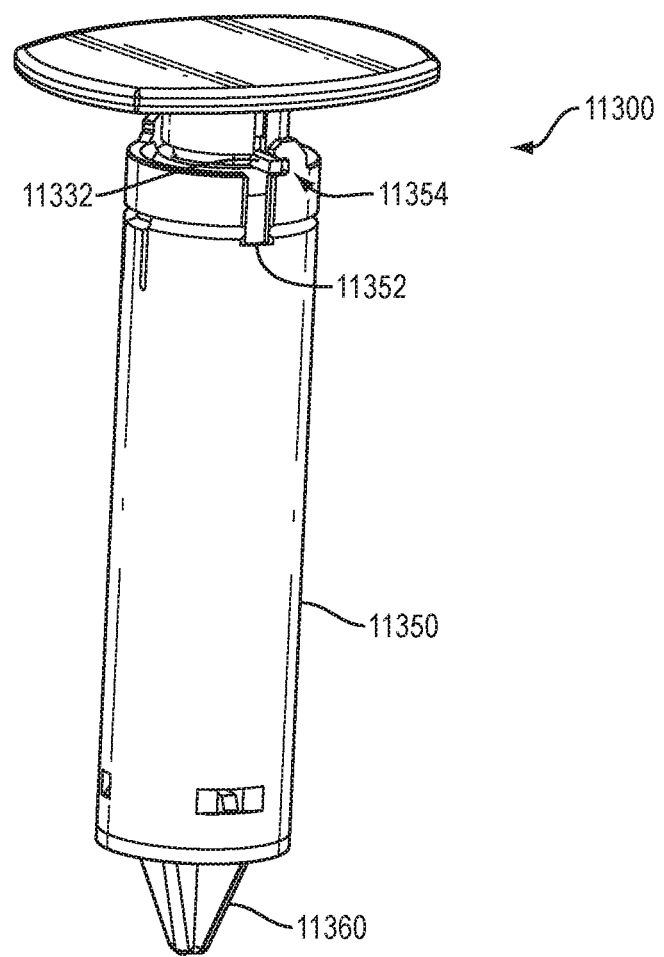
FIG. 18 shows an isometric view of an expanding delivery plunger according to at least one embodiment of the present invention.
Figure 20A:
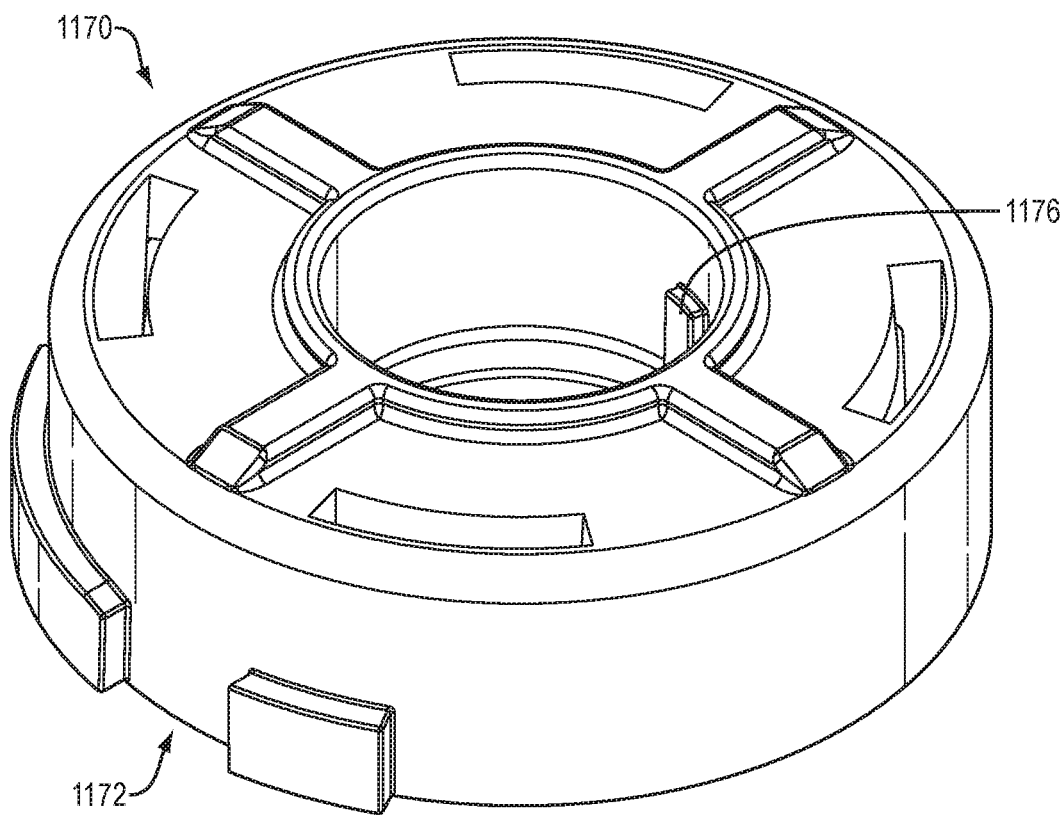
FIG. 20A shows an isometric view of a lockout ring according to at least one embodiment of the present invention.
Figure 20B:
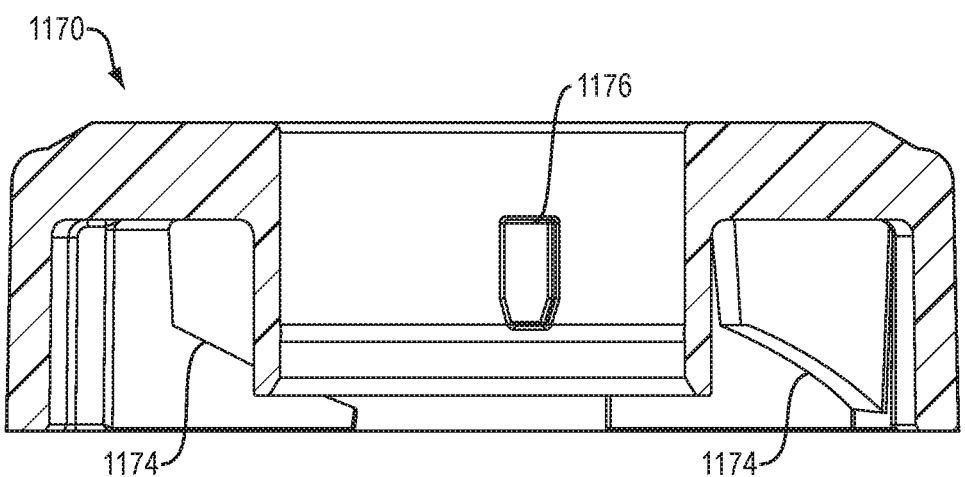
FIG. 20B shows a cross-sectional view of a lockout ring according to at least one embodiment of the present invention.

Another embodiment of an actuating device is shown in FIG. 16 and is further detailed in FIGS. 17-20. The actuating device is configured to engage a mixing device 200 as described above. In the embodiment shown in FIG. 16 trigger member 1120 is configured to be translatable parallel to axis A. In this embodiment trigger member 1120 is configured to be moved in the proximal direction to actuate the mixing device. It is contemplated however that the actuating device may be configured such that distal displacement of trigger member 1120 activates the mixing device. Trigger member 1120 may be engaged with a locking member 1130, which can be seen in FIG. 17, such that axial translation of trigger member 1120 and locking member 1130 are coupled. In an initial configuration, locking member 1130 is engaged with recess 1172 of lockout ring 1170 (shown in FIG. 20), thereby preventing rotation of lockout ring 1170 around axis A. In this position, lockout ring 1170 prevents movement of mixing plunger sleeve 1140. Translation of mixing plunger 1140 may be restricted by interaction of protrusions 1145 with ramped surfaces 1174 of lockout ring 1170 (shown in FIG. 20B). Lockout ring 1170 is also in rotational engagement with outer sleeve 11350 of delivery plunger 11300. Boss 1176 of lockout ring 1170 may be engaged with slot 11352 of outer sleeve 11350.

In at least one embodiment, the delivery plunger is configured such that translation of inner sleeve 11330 is, in an initial configuration, constrained by engagement with outer sleeve 11350. In the embodiment shown in FIG. 18, extension 11332 of inner sleeve 11330 is engaged with recess 11354 of outer sleeve 11350. In this configuration inner sleeve 11330 is restricted from axial translation with respect to outer sleeve 11350 and hence, extension biasing member 11370, disposed between seal engaging member 11360 and inner sleeve 11330, is restricted from decompressing or de-energizing. Intermediate sleeve 11340, located between inner sleeve 11330 and outer sleeve 11350 is also prevented from axial translation. In this embodiment, seal engaging member 11360, outer sleeve 11350, intermediate sleeve 11340, inner sleeve 11330, and biasing member 11370 may be assembled independently from the other components of the actuating device. This may offer advantages in production and scheduling.

In an initial configuration, mixing plunger 1140 is prevented from axial translation by engagement of protrusions 1145 with ramped surfaces 1174 of lockout ring 1170. Inner sleeve 11330 is prevented from translating with respect to outer sleeve 11350 by engagement of extension 11332 with recess 11354. The user may activate translation of mixing plunger sleeve 1140 and/or expansion of delivery plunger 11300 by translating trigger member 1120 such that locking member 1130 disengages recess 1172 of lockout ring 1170. This allows rotation of lockout ring 1170. Rotation of lockout ring 1170 may be caused and/or initiated by a biasing member, such as mixing biasing member 1150, which may be rotationally biased such that in de-energizing the biasing member causes rotation of lockout ring 1170. Alternatively, or additionally, interaction of protrusions 1145 of mixing plunger sleeve 1140 may impart rotation to lockout ring 1170. Rotation of lockout ring 1170 may further allow expansion of delivery plunger 11300, caused by decompression or de-energizing of biasing member 11370. Lockout ring 1170 may be in rotational engagement with outer sleeve 11350 such that rotation of lockout ring 1170 is transferred to outer sleeve 11350. This engagement may be between bosses 1176 of lockout ring 1170 and slots 11352 of outer sleeve 11350. Rotation of outer sleeve 11350 decouples it from inner sleeve 11330 by disengaging recess 11354 from extension 11332 of inner sleeve 11330. After disengagement inner sleeve 11330 is able to translate with respect to outer sleeve 11350 and may be caused to translate by decompression or de-energizing of biasing member 11370. Thus, translation of trigger member 1120 causes and/or initiates translation of mixing plunger sleeve 1140 and expansion of the delivery plunger.

After expansion of delivery plunger 11300, lockouts, as described above, may be configured to substantially prevent the sleeves of the delivery plunger from translating with respect to one another. This allows the delivery plunger to act as a substantially rigid plunger during delivery of the mixed contents contained in the inner chamber.

Figure 21:
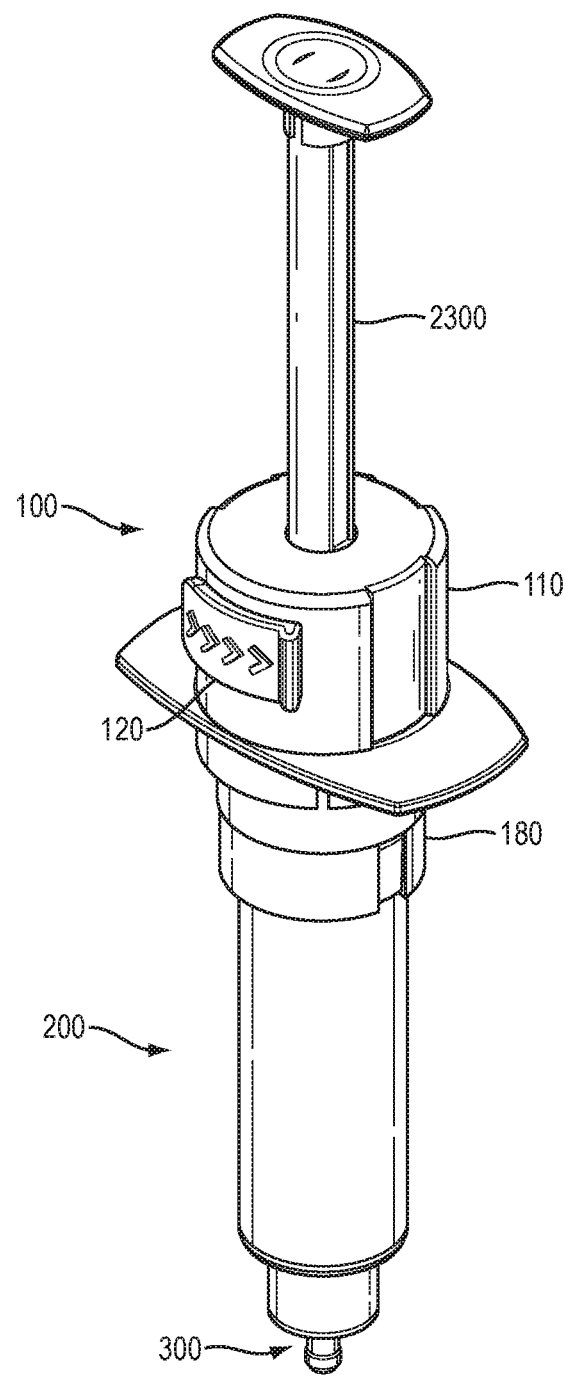
FIG. 21 shows an isometric view of a mixing device with a rigid delivery plunger according to at least one embodiment of the present invention.

Alternatively, an actuating device may comprise a delivery plunger which does not require expansion prior to delivery of the mixed contents contained in the inner chamber. In these embodiments, the delivery plunger may be similar to that shown in FIG. 21, in which the shaft 2300 of the delivery plunger comprises a single component. In the embodiment shown in FIG. 21, actuation of trigger member 120 causes and/or allows translation of the mixing plunger, thereby mixing the contents contained in the outer chamber with the contents of the inner chamber. Depression of the delivery plunger causes the mixed contents of the inner chamber to exit through the end fitment. In some embodiments, one or more safety mechanisms may be used to prevent premature or unintentional depression of the delivery plunger.

In some embodiments, actuating device 100 is configured to prevent or reduce the possibility of inadvertent or unintentional translation of the trigger member. For example, a safety member may be positioned such that it must be removed by the user prior to translation of the trigger member. The safety member may be engaged with first opening 111 of upper housing 110 such that it restricts translation of the trigger member. Alternatively, or additionally, the trigger member may require a two-step motion to allow translation. For example, the user may be required to depress the trigger member prior to or concurrently with rotational and/or axial translation. Alternatively, the user may be required to pull the trigger member outward prior to rotational and/or axial translation. Additionally, or alternatively, the trigger member or locking member may be configured to have a detent or similar feature which initially prevents rotational and/or axial motion of the trigger member.

In addition to the axial translation of the trigger member described above, additional methods of activation are envisioned. For example, the trigger member may be a button that, upon depression by the user, causes and/or allows rotation of the lockout ring. Alternatively, the trigger member may be a toggle switch such that, by toggling the trigger member from one position to another, the user may initiate rotation of the lockout ring.

In at least one embodiment of the present invention, the actuating device 100 is utilized with an automatic mixing syringe 10 having a needle retraction mechanism.

A preferred needle retraction mechanism comprises a needle assembly 300 comprising one or more biasing members that facilitate needle retraction. As shown in FIGS. 22A-D, in contrast to an embodiment to be described hereinafter, the needle assembly 300 comprises one or more biasing members 340 actuatable by delivery plunger 1300, wherein there is no engagement between delivery plunger seal 160 and the retractable needle 310, release of a biasing member 340 in the needle assembly 300 causes retraction of the retractable needle 310. The embodiment shown in FIGS. 22A and 22B has a single biasing member 340 (e.g., a single spring) in a sleeve 350 in the needle assembly 300; the embodiment shown in FIGS. 22C-D has a biasing member 340 comprising springs 342, 344.

FIGS. 22A and 22B show cross-sectional views according to one embodiment of the present invention. The needle assembly 300 includes retractable needle 310 comprising needle-over-mold ("NOM") 322, cannula 311, and, optionally, a needle blocking mechanism adapted to block the cannula 311 following retraction. In the illustrated embodiment, the needle blocking mechanism includes a clip 324. Clip 324 may initially slidably or removably engage NOM 322 such as, for example, at an engagement between clip arms 324A and NOM engagement surface 322A. Upon retraction of the cannula 301 and axial translation in the proximal direction of NOM 322, the clip arms 324A may flex inwards (i.e., towards the axis A) to contact NOM tip 322D in a needle blocking configuration. Such a needle blocking configuration prevents axial travel in the distal direction after retraction and retains the cannula 311 substantially within the barrel tip 330 and/or the barrel of the syringe 10.

Turning to FIG. 22A, the needle assembly 300 further includes an actuable locking arrangement disposed to maintain a biasing member 340 in an energized position until actuated by the actuator subassembly to retract the cannula 311. In the illustrated embodiment, the barrel tip 330 includes a spring guide 330A. In order to maintain the biasing member 340 in its initial energized position, the NOM 322 may initially be disposed in engagement with the barrel tip 330, sandwiching the energized biasing member 340 between one or more ledges 322C of the NOM 322 and an engagement surface 330C of the barrel tip 330. In one such embodiment of the actuable locking arrangement, the spring guide 330A of the barrel tip 330 may include one or more locking recesses or locking ledges 330B adapted to receive, for example, locking prongs 322B of NOM 122. As will be described further below, upon substantial completion of drug delivery through the fluid path, i.e., needle 310, the actuable locking arrangement may be actuated by the actuator subassembly to cause the locking prongs 322B to move inward and release from the locking recesses 330B of the barrel tip 330 to then permit the biasing member 340 to deenergize, exerting a force on the ledge(s) 322C of the NOM 322 to retract the needle 310.

The actuator subassembly 370 is disposed to actuate the actuable locking arrangement to permit the biasing member 340 to deenergize, retracting the needle 310. In the illustrated embodiment, the actuator subassembly 370 includes a needle seal 316, a push bar 312, and an actuator 314. In some embodiments, the push bar 312 is slidably disposed relative to the needle seal 316. In at least one embodiment, push bar 312 resides at least partially within a proximal end of the needle seal 316 and in contact with actuator 314 which resides distal to needle seal 316. Depression of the push bar in such a configuration is capable of contacting and depressing (or axially translating in the distal direction) the actuator 314. In at least an initial configuration, such as for needle insertion into the body of a user, the actuator subassembly 310 may reside proximal to and either in contact with or adjacent to the needle subassembly 320.

In at least one embodiment, push bar 312 includes a proximal contact surface 312A and one or more force transfer elements 312B that extend through corresponding throughways in the needle seal 316. In assembly, the force transfer element 312B extending through the needle seal 316 engage the actuator 314 such that axial movement of the push bar 312 causes axial movement of the actuator 314. In this regard, the push bar 312 and the actuator 314 may be engaged and coupled together during the assembly process or the components may be disposed such assembly such that some axial movement of the push bar 312 is permitted before it engages and causes axial movement of the actuator 314. It is noted that the needle seal 316 may additionally include an opening 316A through which the proximal end of the cannula 311 extends to establish a path for drug delivery.

The actuator 314 includes one or more actuating surfaces disposed to engage and actuate the actuable locking arrangement to actuate the needle retraction mechanism 311. To facilitate operation, in the illustrated embodiment, the actuating surfaces are sloped and disposed to engage corresponding sloped surfaces 322E of the locking prongs 322B of the NOM 322. In this way, the axial movement of the actuator 314 causes the actuating surfaces to slide along the sloped surfaces 322E of the locking prongs 322B to urge the locking prongs 322B radially inward, causing disengagement of the locking prongs 322B from the locking recesses 330B of the barrel tip 330. As a result, the biasing member 340 is permitted to at least partially deenergize, retracting the cannula 311.

In other words, in operation, the delivery plunger seal 160 (not shown) is caused to contact push bar 312. As a result, further depression of the plunger seal 160 during drug delivery causes axial translation of the push bar 312 in the distal direction at least partially through, or further through, needle seal 316. With the push bar 312 in contact with the actuator 314, axial translation of the push bar 312 results in axial translation of the actuator 314. Axial translation of the actuator 314 causes contact with, and flexion of, locking prongs 322B of NOM 122 to disengage the locking prongs 322B from the corresponding locking recesses 330B of the spring guide 330A.

Upon disengagement of the locking arrangement between the locking prongs 322B from the corresponding locking recesses 330B, biasing member 340 is permitted to expand in the proximal direction from its initial energized state to a reduced or de-energized state. This expansion in the proximal direction of the biasing member 340 pushes upon a ledge 322C of NOM 322 causing NOM 322 and cannula 311 to translate in the proximal direction to a retracted state. As described above, upon retraction of the needle 101 and axial translation in the proximal direction of NOM 322, the clip arms 324A may flex inwards (i.e., towards the axis A) to contact NOM tip 322D in a needle blocking configuration. Such a needle blocking configuration prevents axial travel in the distal direction after retraction and retains the needle 310 substantially within the barrel tip 330 and/or the barrel of the syringe. In at least one embodiment of the present invention, push bar 312 and actuator 314 are a unified or single component.

Figures 22C, 22D:
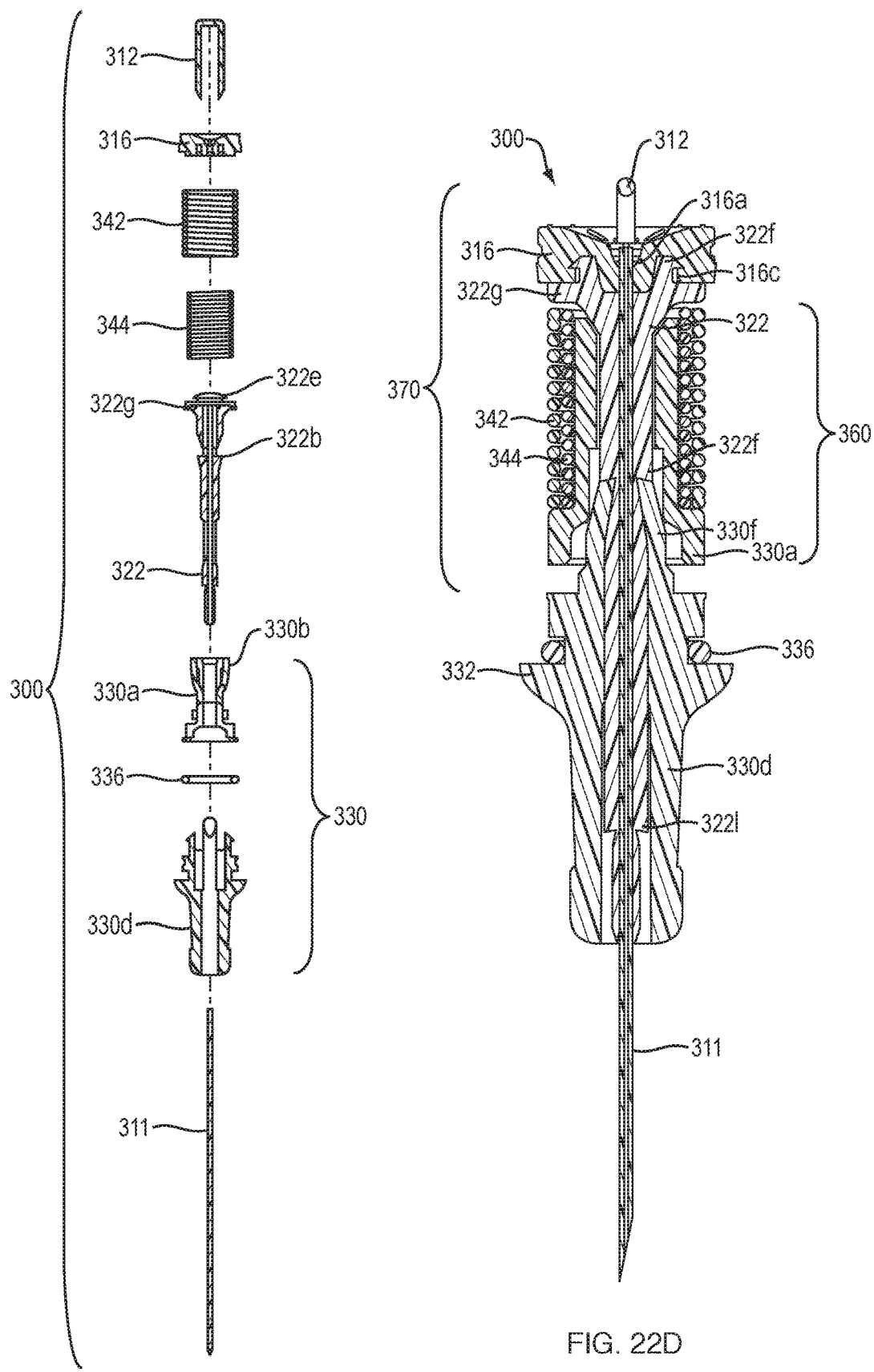
FIG. 22C shows an exploded sectional view of an embodiment of a needle retraction mechanism comprising a needle assembly having a biasing member comprising first and second springs.
FIG. 22D shows a sectional view of an embodiment of a needle retraction mechanism comprising a needle assembly having a biasing member comprising first and second springs.

Turning to FIGS. 22C-D, there is shown another embodiment of needle assembly 300 that includes a barrel tip 330 and a needle subassembly 320, a needle retraction subassembly 360, and an actuator subassembly 370. The needle subassembly 320 includes a cannula 311 and a needle-overmold (NOM) 322. The actuator subassembly 370 includes a needle seal 316, and a push bar 312. The needle subassembly 320 is engaged with the needle seal 316 with a proximal end of the cannula 311 extending through an opening 316A in the needle seal 316. The NOM 322 may be securely coupled to the needle seal 316 in any appropriate manner. For example, in the illustrated embodiment, the NOM 322 includes a plurality of flanges, a first of such flanges 322F engaging an internal flange 316C of the needle seal 316, and a second of said flanges 322G being disposed along a lower surface of the needle seal 316. Further features of the NOM will be described below with regard to the relationship of the needle retraction subassembly 360 and the actuator subassembly 370.

The push bar 312 includes a proximal contact surface 312A and at least one depending force transfer element 312B. Here, a pair of force transfer elements 312B extends through throughways in the needle seal 316. In assembly, the proximal contact surface 312A is disposed proximal the needle seal 316. In contrast to the embodiment in FIGS. 22A and 22B, however, the force transfer element 312B of the push bar 312 includes actuating surfaces, here, angled surfaces. In other words, this embodiment does not include a separate actuator. Rather, the push bar 312 and actuator are a unitary component.

The needle retraction subassembly 360 includes at least one biasing member 340 and an actuable locking arrangement. In this embodiment, the biasing member 340 includes a pair of springs 342, 344. While the springs 342, 344 are disposed in parallel and the support structure is such that they move toward a deenergized position simultaneously, the springs 342, 344 could alternately be disposed and supported such that they move toward a deenergized position in series. Whether disposed in series or in parallel, the inclusion of two or more springs may provide certain advantages in reducing the size of the overall package of the barrel adapter 350. It will be appreciated, however, that supporting the springs in parallel 342, 344 may further enhance these advantages.

In this embodiment, the barrel tip 330 includes multiple components. That is, the spring guide 330A is formed separately from the tip portion 330D, the spring guide 330A and the tip portion 330D being coupled together during assembly. The biasing members 340, or springs 342, 344, may be received around the spring guide 330A. Inserting the assembly of the needle subassembly 320 and the actuator subassembly 310 into the spring guide 330A, the needle subassembly 320 and the spring guide 330A may be coupled together to retain the biasing members 340 in an energized position between engagement surface 330C and ledge 322C. In contrast to the first embodiment, in this embodiment, the spring guide 330A includes at least one locking prong 330B, here, a pair of locking prongs 330B, and the NOM 322 includes a locking ledge 322B. It will thus be appreciated that when the push bar 312 is contacted by the plunger seal 160 (not shown) at the end of administration of medication, the actuating surfaces of the push bar 312 push the locking prongs 330B of the spring guide 330A outward, disengaging them from the locking ledge 322B of the NOM 322. As a result, the biasing members 340 are permitted to release energy to retract the needle subassembly 320 into the barrel. In such embodiments, the trigger member 120 does not need to move substantially in the proximal direction to enable retraction of needle subassembly 320 because the push bar 312 activates retraction of the needle subassembly directly into the inner barrel 210.

Figure 23:
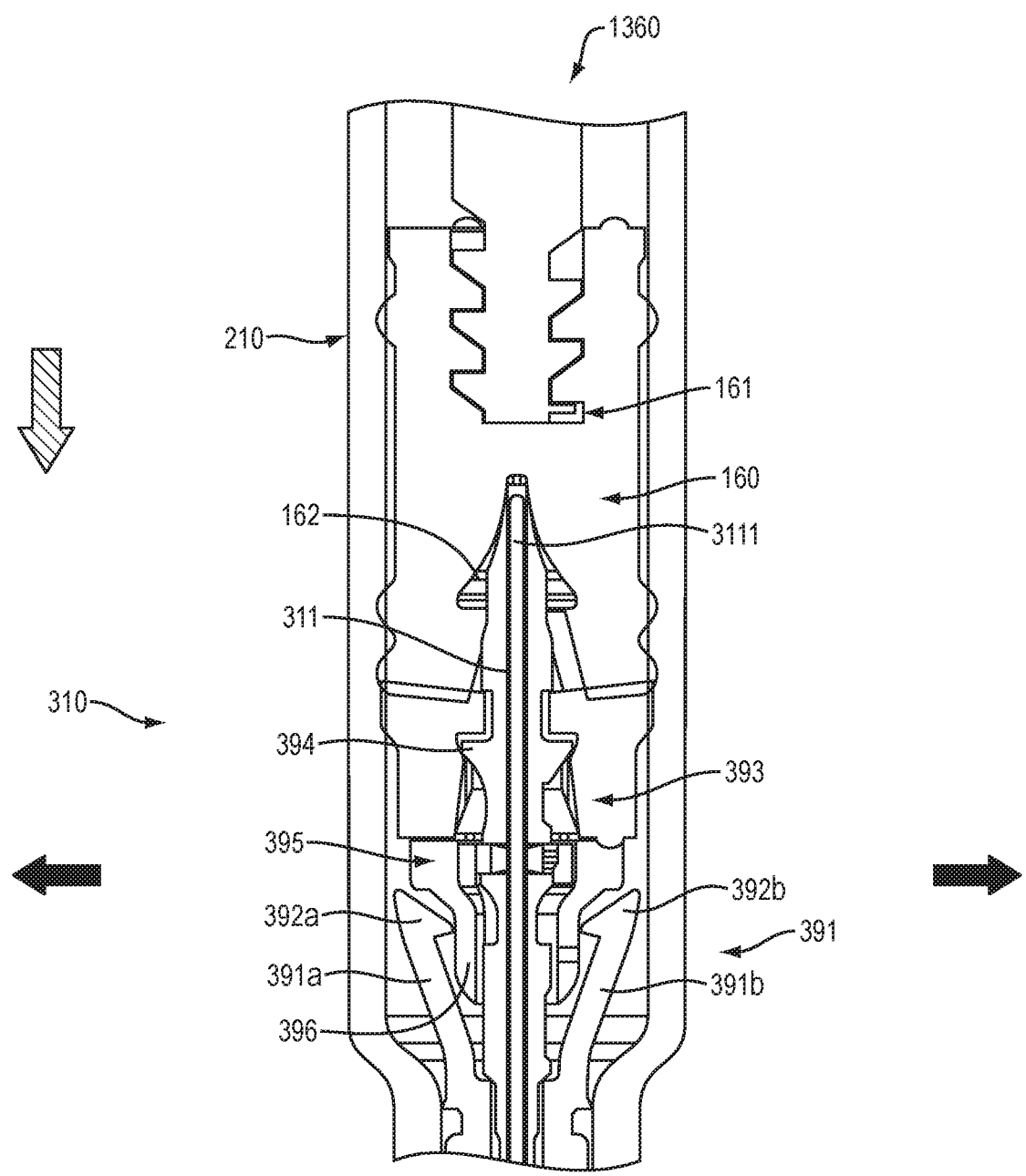
FIG. 23 shows an alternative embodiment of a needle assembly comprising a retractable needle engageable by a delivery plunger seal.

In an alternative embodiment, the retractable needle 310 is retracted by engagement with the delivery plunger seal 160, whereby biasing member 150 of actuation device 100 facilitates retraction of the retractable needle 310. In the particular embodiment shown in FIG. 23, delivery plunger 1300 comprises seal-engaging member 1360, which in this embodiment has a screw threaded projection, which engages a complementary, screw-threaded recess 161 of delivery plunger seal 160. In this embodiment where the retractable needle 310 is retracted by engagement with the delivery plunger seal 160, the delivery plunger seal 160 further comprises needle-engaging portion or recess 162. In at least one embodiment, needle assembly 300 comprises retractable needle 310 comprising cannula 311 and needle body 394, retainer 391 having arms 391A, B and hook-ends 392A, B, needle seal 393 and ejector 395 having ejector ring 396. The needle retraction mechanism shown in FIG. 23 is essentially similar to that described in WO2011/075760. During delivery of fluid contents, delivery plunger 1300 and coupled delivery plunger seal 160 moves axially through inner chamber 230 in the direction of the hatched arrow in FIG. 23. Delivery plunger seal 160 bears against needle seal 314, which in turn bears against ejector 395. Further to this, ejector ring 396 moves hook-ends 392A, B of arms 391A, B of retainer 391 radially outwardly in the direction of the solid arrows in FIG. 23, thereby disengaging needle body 394 from retainer 390 to release retractable needle 310 for subsequent retraction. At this point, needle-engaging portion or recess 162 of delivery plunger seal 160 has engaged retractable needle body 394 and received fluid end 3111 of cannula 311. This effectively couples retractable needle 310 to delivery plunger seal 160 and delivery plunger 1300.

In order for retractable needle 310 to retract at the end of delivery of fluid contents, biasing member 150 must de-energize from its partially or reduced energized state. As hereinbefore described, the biasing member 150 is initially utilized to depress the sleeve 140 (i.e., axially translate in the distal direction) to facilitate the mixing of the first and second substances. Upon suitable activation of the retraction mechanism, such as by capture of the retractable needle 310 as described herein and in WO2011/075760, the biasing member 150 can also be utilized to retract the retractable needle 310 (axially translate in the proximal direction). This disengagement allows partially compressed biasing member 150 to further decompress and push against upper housing 110 to thereby push against and retract plunger 1300. Delivery plunger seal 160 coupled to retractable needle 310 is axially translated in the proximal direction by decompression of the biasing member 150, thereby retracting retractable needle 310. Upper housing 110 may be caused to translate axially in the proximal direction and retract the delivery plunger 130, delivery plunger seal 160 and retractable needle 310 connected thereto. Retainer 390, ejector 395 and needle seal 393 remain at the distal end of inner chamber 230. At the end of retraction of the plunger 1300, delivery plunger seal 160 and retractable needle 310, the upper housing 110 and delivery plunger 1300 (and associated components connected thereto) may be locked out. In addition to retraction of the needle into the barrel(s) of the mixing device, this lockout prevents reuse or tampering of the automatic mixing syringe 10 and makes it safe to dispose.

It will be appreciated from the foregoing that the actuating device, automatic mixing device and syringe disclosed herein provide an efficient and easily-operated automatic system for mixing multiple substances prior to delivery by the syringe. There is no need to rotate or otherwise orient the inner and outer barrels prior to use to open or align fluid pathways, unlike in many prior art mixing devices such as those previously described. The positioning of the distal seal relative to the vents in the outer barrel and the apertures in the inner barrel keeps the contents of the mixing device sterile while providing adequate venting, which is in contrast to many prior art mixing devices such as previously described.

Assembly and/or manufacturing of the actuating device, automatic mixing device, retractable syringe, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization fluids and processes may be employed during the manufacture of the novel components and devices. To add the one or more apertures to the inner barrel, known drilling or boring methodologies such as mechanical or laser drilling may be employed. Furthermore, known sterilization processes may be employed at one or more of the manufacturing or assembly stages to ensure the sterility of the final product.

In yet another aspect, the invention provides a method of assembling a syringe comprising an automatic mixing device including the step of removably mounting an actuating device to a mixing device of the syringe so that a mixing plunger sleeve of the actuating device is operable to depress a mixing plunger seal of the mixing device. In one embodiment, the method includes the step of releasably connecting or coupling a housing of the actuating device to an outer barrel of the mixing device. In one embodiment, the method further includes, prior to step (i), affixing a vent cap comprising the one or more vents to a portion of the inner barrel that is located distally of the one or more apertures. Preferably, the distal end of the outer barrel is connected to the vent cap. In a further embodiment, the method further includes the step of attaching a sealing membrane to the proximal end of the inner barrel of the mixing device prior to attachment of the actuating device to the mixing device. In a preferred embodiment, the sealing membrane is attached such that it is at least partially pierced or penetrable by operation of the delivery plunger. In another embodiment, the sealing membrane is attached in a manner such that it is removed automatically by operation of the mixing plunger sleeve of the actuating device, i.e., axial translation of the sleeve in the distal direction. Preferably, the method further includes the step of inserting a needle assembly into the inner chamber located distally of the one or more apertures.

In a further aspect, the invention provides a method of manufacturing a syringe including the step of removably mounting an actuating device to a mixing device mounted to a syringe.

In a still further aspect, the invention provides a method of operating a syringe comprising an automatic mixing device, said method including the steps of:
(i) operating an actuating device of the automatic mixing device to facilitate mixing a plurality of substances, wherein operation of the actuating device removes a removable membrane from attachment to the mixing device;
(ii) connecting a plunger of the actuating device to a delivery plunger seal of the mixing device;
(iii) operating the plunger to deliver the substances mixed at step (i) to a recipient.

In one embodiment, the method includes the step of expanding one or more telescoping sleeves of the plunger prior to step (iii). Expansion of the plunger may occur between steps (i) and (ii) in at least one embodiment or between steps (ii) and (iii) in other embodiments of the invention.

In an alternative embodiment, a method of operating a syringe comprising an automatic mixing device includes the steps of:

(iv) operating an actuating device of the automatic mixing device to facilitate mixing a plurality of substances;
(v) operating a plunger of the actuating device to pierce a sealing membrane to engage a delivery plunger seal of the mixing device;
(vi) operating the plunger to deliver the substances mixed at step (i) to a recipient.

The method may further include the step of expansion of one or more telescoping sleeves of the plunger prior to step (iii). Expansion of the plunger may occur between steps (i) and (ii) in at least one embodiment or between steps (ii) and (iii) in other embodiments of the invention.

In at least one embodiment, the method of operating a syringe comprising an automatic mixing device further includes: (iv) activating a needle retraction mechanism to retract the needle into the syringe. Preferably, the activation of the needle retraction mechanism occurs after substantially all of the substances are delivered to the recipient.

As discussed above, a number of aspects of the present invention may be facilitated by separate components. Alternatively, one or more components of the present invention may be a unified component and/or the functions of such one or more components may be accomplished by a unified component. For example, the trigger member, and several other components, can be single unified components or made up of smaller sub-components. It is readily understood by one having ordinary skill in the art that such components may be unified components or comprised of separate sub-components, such as for manufacturability, while remaining within the breadth and scope of the presently claimed invention.

A number of known filling processes and equipment may be utilized to achieve the filling steps of the syringe manufacturing process. In one embodiment, the second fluid substance may be filled as a liquid substance and lyophilized in situ using certain barrel heat transfer equipment. The needle assembly, delivery plunger, and other components described in these manufacturing and assembly processes may be as described above or may be a number of similar components which achieve the same functionality as these components.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

What is claimed is:

1. An actuating device, comprising:
    a lower housing configured to be releasably connectable to a mixing device for a syringe;
    an upper housing engaged with the lower housing;
    a trigger member;
    a lockout ring;
    a mixing biasing member;
    a delivery plunger;
    a plunger biasing member; and
    a mixing plunger releasably engaged with the trigger member in an initially locked state and engageable with at least one seal of the mixing device, wherein the trigger member is operable to initiate decompression of the mixing biasing member and engagement of the mixing plunger with the at least one seal of the mixing device and wherein the trigger member is further operable to initiate decompression of the plunger biasing member and expansion of the delivery plunger from an initial, collapsed configuration to an expanded configuration.

2. The actuating device of claim 1, wherein the lockout ring is rotatably engaged with the trigger member and configured to permit decompression of the mixing biasing member upon rotation.

3. The actuating device of claim 1, wherein the mixing plunger comprises one or more sleeve members configured to bear upon and axially translate the at least one seal of the mixing device.

4. The actuating device of claim 1, wherein the delivery plunger comprises one or more telescoping aspects.

5. The actuating device of claim 1, wherein the delivery plunger comprises a plunger cap including a flange initially engaged with a protrusion of the lockout ring, the flange configured to disengage from the protrusion upon rotation of the lockout ring.

6. The actuating device of claim 1, wherein the actuating device is mountable or mounted to the mixing device in an initially locked state.

7. The actuating device of claim 2, wherein the mixing plunger comprises one or more protrusions initially engaged with a surface of the lockout ring, the protrusions configured to disengage from the surface upon rotation of the lockout ring.

8. An automatic mixing device of a syringe, comprising:
    the actuating device of claim 1; and
    a mixing device comprising:
        an outer barrel and an inner barrel in a substantially coaxial relationship, and
        at least one seal located in an annular space between the inner barrel and the outer barrel, the at least one seal axially moveable within the annular space.

9. The automatic mixing device of claim 8, further comprising a sealing membrane configured to maintain sterility of the mixing device and removable by or during operation of the actuating device.

10. The automatic mixing device of claim 8, wherein the outer barrel comprises a barrel extension to which the actuating device is removably mountable or mounted.

11. The automatic mixing device of claim 8, wherein the inner barrel comprises one or more fluid paths configured to provide fluid communication between an inner chamber of the inner barrel and an outer chamber located in the annular space between the inner barrel and the outer barrel.

12. The automatic mixing device of claim 8, further comprising at least one vent in fluid communication with the annular space, the vent operable to facilitate exit of air from the annular space to the atmosphere when the mixing plunger and the at least one seal are axially translated within the annular space.

13. The automatic mixing device of claim 9, wherein sleeve members of the mixing plunger are configured to at least partially remove or puncture the sealing membrane upon axial translation.

14. The automatic mixing device of claim 9, wherein a distal tip of the delivery plunger is configured to pierce the sealing membrane upon axial translation.

15. The automatic mixing device of claim 11, wherein the mixing device comprises at least a first mixing substance in the outer chamber and a second mixing substance in the inner chamber, the fluid path configured to permit the first mixing substance to enter the inner chamber upon displacement of the at least one seal.

16. The automatic mixing device of claim 15, wherein at least one of the first mixing substance and the second mixing substance is a fluid and at least one of the first mixing substance and the second mixing substance comprises an active pharmaceutical, the automatic mixing device enabling reconstitution or mixing of the active pharmaceutical.

17. An automatic mixing syringe, comprising:
    an end fitment;
    a mixing device comprising:
        an outer barrel and an inner barrel in a substantially coaxial relationship, and
        at least one seal located in an annular space between the inner barrel and the outer barrel, the at least one seal axially moveable within the annular space; and
    an actuating device comprising:
        a lower housing configured to be releasably connectable to a mixing device for a syringe,
        an upper housing engaged with the lower housing,
        a trigger member,
        a lockout ring,
        a mixing biasing member,
        a delivery plunger,
        a plunger biasing member, and
        a mixing plunger releasably engaged with the trigger member in an initially locked state and engageable with the least one seal of the mixing device, wherein the trigger member is operable to initiate decompression of the mixing biasing member and engagement of the mixing plunger with the at least one seal of the mixing device, the mixing plunger axially translating the at least one seal within the annular space, and wherein the trigger member is further operable to initiate decompression of the plunger biasing member and expansion of the delivery plunger from an initial, collapsed configuration to an expanded configuration.

* * * * *